__(12)__ United States Patent
Balasubramanian et al.

US008889950B2

(10) Patent No.: US 8,889,950 B2
(45) Date of Patent: Nov. 18, 2014

(54) REPRESSION OF ATGLR3.2 INCREASES PLANT BIOMASS

(75) Inventors: Sivasubramanian Balasubramanian, Tamil Nadu (IN); Frank J. Turano, Baltimore, MD (US)

(73) Assignee: The George Washington University, Washington, DC (US)

( * ) Notice: Subject to any disclaimer, the term of this patent is extended or adjusted under 35 U.S.C. 154(b) by 1266 days.

(21) Appl. No.: 11/829,898

(22) Filed: Jul. 28, 2007

(65) Prior Publication Data

US 2009/0265805 A1    Oct. 22, 2009

Related U.S. Application Data

(60) Provisional application No. 60/820,763, filed on Jul. 28, 2006.

(51) Int. Cl.
*C12N 15/87* (2006.01)
*C12N 15/82* (2006.01)
*C12N 15/113* (2010.01)
*C07K 14/705* (2006.01)

(52) U.S. Cl.
CPC ...... *C07K 14/70571* (2013.01); *C12N 15/8261* (2013.01)
USPC ............................ 800/285; 800/287; 800/290

(58) Field of Classification Search
USPC ...................... 435/6.1, 69.1, 468, 419, 320.1; 536/23.6; 800/278, 295; 530/370
See application file for complete search history.

(56) References Cited

U.S. PATENT DOCUMENTS

| | | | |
|---|---|---|---|
| 5,824,867 A | 10/1998 | Coruzzi et al. | |
| 5,959,174 A | 9/1999 | Coruzzi et al. | |
| 5,981,703 A | 11/1999 | Coruzzi et al. | |
| 6,084,084 A * | 7/2000 | Stormann et al. | 536/23.5 |
| 6,177,275 B1 | 1/2001 | Coruzzi et al. | |
| 6,451,546 B1 | 9/2002 | Coruzzi et al. | |
| 6,797,692 B1 | 9/2004 | Ikonomidou | |
| 6,822,079 B2 | 11/2004 | Coruzzi et al. | |
| 6,844,486 B1 | 1/2005 | Xie et al. | |
| 6,846,969 B2 | 1/2005 | Donn et al. | |
| 6,864,405 B1 | 3/2005 | Coruzzi et al. | |
| 6,911,576 B1 | 6/2005 | Kirby et al. | |
| 2003/0022305 A1 | 1/2003 | Coruzzi et al. | |
| 2003/0233670 A1 | 12/2003 | Edgerton et al. | |
| 2006/0041962 A1 | 2/2006 | Inze et al. | |
| 2006/0142395 A1 | 6/2006 | Koulen et al. | |
| 2009/0210967 A1 | 8/2009 | Turano et al. | |

FOREIGN PATENT DOCUMENTS

| | | |
|---|---|---|
| WO | WO 95/09911 | 4/1995 |
| WO | 9639805 A1 | 12/1996 |
| WO | WO 97/30163 | 8/1997 |
| WO | WO 00/34772 | 6/2000 |
| WO | WO 00/73244 | 12/2000 |
| WO | WO 01/55433 | 8/2001 |
| WO | WO 02/02776 | 1/2002 |
| WO | WO 02/098227 | 12/2002 |
| WO | WO 03/060133 | 7/2003 |
| WO | 2004035798 | * 4/2004 |

OTHER PUBLICATIONS

Arteca and Arteca 2000 Physiologia Plantarum 108: p. 188-193.*
Kim et al 2001 Plant Cell and Physiology 42:1 p. 74-84.*
J. Kang and F.J. Turano, The putative glutamate receptor 1.1 (AtGLR1.1) functions as a regulator of carbon and nitrogen metabolism in Arabidopsis thaliana, PNAS, May 27, 2003, vol. 100, pp. 6872-6877, www.pnas.org/cgi/doi.
J. Kang, S. Mehta, and F.J. Turano, The putative glutamate receptor 1.1 (AtGLR1.1) in Arabidopsis thaliana regulates abscisic acid biosynthesis and signaling to control development and water loss, Plaint Cell Physiol., 2004, vol. 45, No. 10, pp. 1380-1389.
Glutamate-receptor genes in plants, Scientific Correspondence, Nature, vol. 396, Nov. 12, 1998, pp. 125-126, listed on ISR as GenBank Accession # AF079998 "Arabidopsis thaliana putative glutamate receptor (GLR1) mRNA, complete cds." (Jan. 26, 1999).
S.A. Kim, J.M. Kwak, S.K. Jae, M.H. Wang and H.G. Nam, Overexpression of the AtGluR2 Gene Encoding an Arabidopsis Homolog of Mammalian Glutamate Receptors Impairs Calcium Utilization and Sensistivity to Ionic Stress in Transgenic Plants, Plant Cell Physiology, vol. 42, No. 1, pp. 74-84, 2001, listed on ISR as GenBank Accession # AF159498, "Arabidopsis thaliana putative glutamate receptor like-protein (GLUR2) mRNA, complete cds." (Feb. 28, 2001).
Written Opinion dated May 3, 2012, cited in International Application No. PCT/US2009/061399.

* cited by examiner

*Primary Examiner* — David T Fox
*Assistant Examiner* — Matthew Keogh
(74) *Attorney, Agent, or Firm* — Blank Rome LLP

(57) ABSTRACT

The present invention relates to methods that may be used to improve or modify nutrient sensing, absorption, metabolism, root growth, stomatal conductance, N use efficiency, C and N metabolism, plant biomass production and seed yield. More specifically, this invention is related to the glutamate receptors (GLRs) and their role(s) in nutrient sensing, metabolism, regulation of growth, development, and yield.

13 Claims, 11 Drawing Sheets

 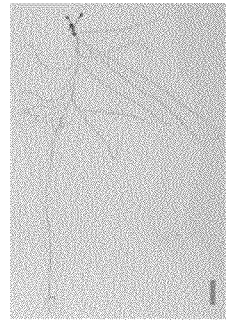 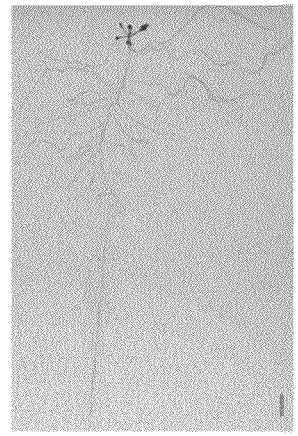
FIG. 3A  FIG. 3B  FIG. 3C
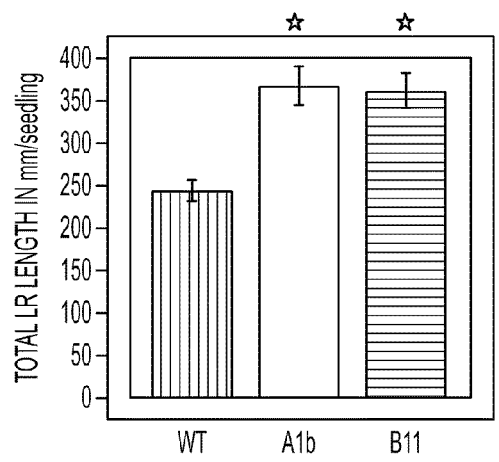 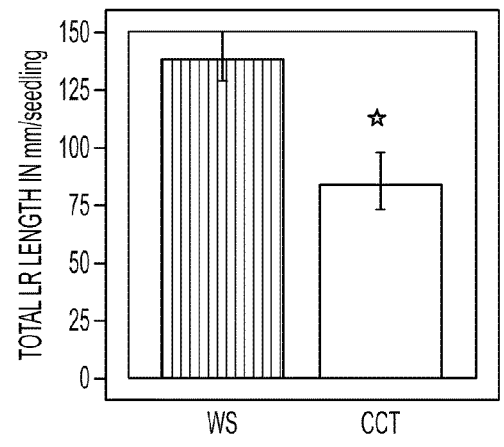
FIG. 3D  FIG. 3E

DNQX-400

DMSO

DR5::GUS DNQX

DR5::GUS DMSO

AsAtGLR3.2 PLANTS SHOW HIGHER STOMATAL CONDUCTANCE

*AntiAtGLR3.2* PLANTS ARE LARGE INDICATING HIGHER BIOMASS PRODUCTION (SEQ ID NO: 1)
>gi|4185737|gb|AF079998.1|AF079998 Arabidopsis thaliana putative glutamate receptor (GLR1) mRNA, complete cds AAGCGAACGTTACAGAGCTATACAAGAAATTATATGGAGATTCTGTTTTCTATTTCCATTCTTGCTCTTC
TCTTTTCCGGAGTAGTAGCTGCTCCAAGCGACGATGATGTTTTCGAAGAGGTTAGGGTTGGATTGGTGGT
TGACTTGAGTTCTATTCAAGGCAAGATTCTGGAAACTTCTTTTAACTTAGCGCTTTCAGATTTCTATGGC
ATCAACAATGGATACCGAACCAGAGTCTCTGTTTTGGTCAGAGACTCCCAAGGAGACCCGATCATTGCTC
TTGCCGCCGCTACTGATCTTCTCAAAAATGCAAAAGCGGAAGCCATTGTTGGTGCACAATCATTACAAGA
GGCAAAGCTTTTGGCGACGATTAGCGAAAAAGCTAAAGTTCCGGTCATATCTACTTTCTTGCCAAACACG
TTATCTTTGAAGAAATACGATAACTTTATTCAATGGACGCATGATACTACATCAGAGGCTAAGGGAATTA
CAAGTCTCATACAAGATTTCAGTTGTAAATCGGTTGTGGTTATATACGAGGATGCTGATGATTGGAGTGA
GAGTTTGCAAATATTGGTTGAGAATTTTCAAGATAAAGGAATCTATATCGCTCGTTCTGCTTCTTTTGCA
GTCTCATCATCAGGAGAAAATCATATGATGAATCAGCTAAGGAAGCTTAAGGTCTCAAGAGCATCGGTTT
TTGTGGTGCATATGTCCGAGATTCTTGTTTCTCGTCTCTTCCAATGTGTAGAAGTTAGGTTTGATGGA
AGAAGCGTTCGCTTGGATCCTCACTGCAAGAACCATGAACTACTTGGAACATTTTGCAATAACTAGGTCG
ATGCAAGGGGTCATTGGTTTCAAATCTTACATCCCTGTATCTGAAGAAGTTAAGAATTTTACTTCAAGAT
TGAGGAAACGTATGGGAGATGATACAGAAACAGAGCATTCTAGTGTAATCATCGGTTTACGCGCACACGA
TATCGCTTGTATTCTAGCAAATGCAGTAGAGAAGTTCAGTGTAAGTGGTAAAGTTGAAGCATCTTCGAAT
GTATCAGCTGATCTTCTGGATACAATTAGACATAGTAGATTCAAGGGTTTGAGTGGTGACATCCAAATCT
CTGACAACAAATTTATCTCAGAGACATTTGAAATCGTGAATATTGGAAGAGAAAAACAGAGAAGGATAGG
ATTATGGAGTGGTGGTAGTTTTAGCCAAAGAAGACAGATTGTTTGGCCTGGCAGGTCTCGTAAGATCCCA
AGACACCGTGTTTTGGCAGAGAAAGGTGAAAAGAAGGTGCTTAGGGTCTTAGTTACCGCAGGAAACAAGG
TCCCGCATCTAGTGTCGGTGCGTCCTGATCCTGAAACAGGTGTTAATACTGTCTCTGGATTCTGCGTAGA
GGTTTTCAAGACTTGCATTGCTCCTTTTAACTACGAGCTTGAATTCATACCTTACCGTGGAAACAATGAC
AATCTTGCTTATCTACTTTCTACTCAGAGAGACAAGTATGATGCAGCAGTTGGTGATATCACCATCACTT
CCAACAGATCTTTGTATGTTGATTTTACTTTGCCGTACACTGACATTGGTATTGGAATCCTGACAGTAAA
AAAGAAAAGCCAAGGGATGTGGACTTTCTTTGATCCTTTTGAAAAATCCTTGTGGCTAGCGAGTGGAGCT
TTCTTCGTCTTGACCGGGATTGTTGTTTGGTTGGTTGAACGGCCCGTTAATCCGGAGTTTCAAGGCTCTT
GGGGACAACAACTTAGTATGATGCTCTGGTTTGGATTCTCTACCATTGTGTTTGCTCACAGGGAGAAGCT
ACAGAAAATGTCATCAAGATTCTTAGTCATAGTTTGGGTTTTTGTGGTGTTAATATTGACTTCAAGTTAC
AGCGCAAACTTGACATCAACCAAGACCATTTCTCGCATGCAATTAAATCATCAGATGGTTTTCGGGGGAT
CTACGACGTCAATGACTGCGAAGCTCGGATCCATTAATGCAGTTGAGGCCTATGCACAACTTTTGCGAGA
TGGAACTCTTAATCATGTCATCAATGAAATACCTTATCTCAGTATCCTTATCGGAAATTATCCGAATGAT
TTCGTAATGACAGATAGAGTGACTAATACCAATGGCTTTGGCTTTATGTTCCAGAAAGGTTCGGATTTGG
TTCCTAAAGTATCGCGAGAAATCGCGAAGCTAAGATCATTGGGAATGTTGAAAGACATGGAGAAAAAATG
GTTTCAAAAGCTGGATTCACTAAATGTACATTCCAACACTGAGGAAGTTGCCTCTACCAACGACGATGAT
GAGGCATCTAAGCGATTCACCTTCCGTGAGTTGCGCGGTTTGTTCATCATTGCGGGAGCTGCTCATGTTC
TCGTACTAGCCCTACATCTCTTTCATACGCGTCAAGAGGTATCACGACTATGCACCAAACTTCAAAGCTT
CTATAAGTAAAAAGTGATCCATCATTCATAAGCTCTACTATAGCAATTGATGGAGGACTCATAAGTAACA
ACAAAGTACACTTCGAAACAAATGTCACATGTAATACTTGGTTTTTTTCCCGTTTAAATTCACATGTAA
TAATTTAACTCACGTAAATACTAAAGTGATTCACCCAAAAAAAAAAAAAAAA
(SEQ ID NO: 1)
>gi|4185738|gb|AAD09173.1| putative glutamate receptor [Arabidopsis thaliana]
MEILFSISILALLFSGVVAPSDDDVFEEVRVGLVVDLSSIQGKILETSFNLALSDFYGINNGYRTRVSV
LVRDSQGDPIIALAAATDLLKNAKAEAIVGAQSLQEAKLLATISEKAKVPVISTFLPNTLSLKKYDNFIQ
WTHDTTSEAKGITSLIQDFSCKSVVVIYEDADDWSESLQILVENFQDKGIYIARSASFAVSSSGENHMMN
QLRKLKVSRASVFVVHMSEILVSRLFQCVEKLGLMEEAFAWILTARTMNYLEHFAITRSMQGVIGFKSYI
PVSEEVKNFTSRLRKRMGDDTETEHSSVIIGLRAHDIACILANAVEKFSVSGKVEASSNVSADLLDTIRH
SRFKGLSGDIQISDNKFISETFEIVNIGREKQRRIGLWSGGSFSQRRQIVWPGRSRKIPRHRVLAEKGEK
KVLRVLVTAGNKVPHLVSVRPDPETGVNTVSGFCVEVFKTCIAPFNYELEFIPYRGNNDNLAYLLSTQRD
KYDAAVGDITITSNRSLYVDFTLPYTDIGIGILTVKKKSQGMWTFFDPFEKSLWLASGAFFVLTGIVVWL
VERPVNPEFQGSWGQQLSMMLWFGFSTIVFAHREKLQKMSSRFLVIVWVFVVLILTSSYSANLTSTKTIS
RMQLNHQMVFGGSTTSMTAKLGSINAVEAYAQLLRDGTLNHVINEIPYLSILIGNYPNDFVMTDRVTNTN
GFGFMFQKGSDLVPKVSREIAKLRSLGMLKDMEKKWFQKLDSLNVHSNTEEVASTNDDDEASKRFTFREL
RGLFIIAGAAHVLVLALHLFHTRQEVSRLCTKLQSFYK
(SEQ ID NO: 3)

FIG. 14

>gi|13160470|gb|AF159495.1|AF159498 Arabidopsis thaliana putative glutamate receptor like-protein (GLUR2) mRNA, complete cds
GGTGTTTCAGGAACTGATTAAGCCAAAGCTATGTTTTGGGTTTTGGTTCTGTTGAGCTTCATTGTTCTTA
TTGGTGATGGGATGATTTCAGAGGGAGCTGGTTTAAGGCCTCGTTATGTTGATGTTGGAGCAATATTCAG
TTTAGGGACTTTACAGGGTGAAGTTACAAATATTGCTATGAAAGCTGCAGAGGAAGATGTAAATTCTGAT
CCTAGCTTCCTTGGTGGATCAAAATTGCGTATAACGACGTATGATGCAAAGCGTAATGGATTCCTCACCA
TCATGGGAGCTTTGCAATTCATGGAGACTGATGCTGTGGCTATCATTGGTCCTCAGACATCAATAATGGC
TCATGTACTGTCTCATCTTGCAAATGAGCTTAGTGTGCCTATGTTGTCATTCACAGCTTTAGACCCTAGT
CTCTCGGCGCTTCAGTTCCCGTTCTTTGTCCAGACAGCACCTAGTGATCTCTTTCTGATGCGTGCCATTG
CGGAAATGATAAGTTACTACGGTTGGTCAGAGGTGATTGCATTGTATAATGATGATGACAACAGTAGAAA
CGGTATAACAGCTTTAGGCGATGAGCTCGAAGGAAGGCGCTGCAAGATTTCATACAAGGCTGTGCTTCCT
TTGGATGTGGTGATTACGAGTCCTCGTGAGATTATAAATGAGTTGGTTAAGATTCAAGGGATGGAATCTC
GGGTAATCATTGTGAACACTTTCCCTAAAACAGGTAAGAAAATCTTTGAGGAAGCCCAGAAGCTTGGCAT
GATGGAGAAAGGCTATGTTTGGATAGCTACAACTTGGTTGACTTCTCTGTTAGATTCTGTTAACCCGTTA
CCTGCCAAGACTGCTGAATCTCTTAGAGGCGTGCTTACTCTTCGTATTCACACGCCAAATTCAAAAAAGA
AAAAAGATTTCGTGGCACGGTGGAACAAGTTGAGTAACGGGACTGTCGGTTTAAACGTTTATGGTCTCTA
TGCTTATGATACTGTCTGGATCATTGCTCGAGCTGTTAAGAGACTTCTAGATAGCAGAGCTAACATTTCC
TTCTCTAGTGACCCAAAGTTAACCAGCATGAAGGGAGGAGGGTCACTGAATCTAGGTGCATTGAGCATAT
TTGACCAAGGATCACAATTTCTTGATTATATTGTGAATACAAATATGACTGGTGTTACAGGTCAAATACA
GTTTCTTCCTGACAGATCAATGATACAGCCCTCATATGACATCATAAACGTGGTTGATGACGGGTTTAGG
CAGATAGGGTATTGGTCTAACCATTCCGGGCTCTCTATTATACCTCCAGAGTCACTATACAAAAAGCTTT
CAAATCGTTCGAGCTCAAACCAACATCTGAACAATGTGACTTGGCCTGGTGGGACTTCTGAGACACCACG
TGGTTGGGTTTTTCCTAACAACGGGAGACGATTGAGAATCGGTGTACCCGATAGAGCAAGTTTTAAGGAG
TTTGTGTCAAGGTTGGATGGAAGCAACAAAGTGCAAGGGTATGCCATTGATGTCTTTGAAGCTGCGGTAA
AACTGATTTCTTATCCGGTTCCTCATGAGTTCGTCCTATTTGGAGACGGTCTCAAGAACCCAAACTTCAA
TGAATTTGTCAACAATGTCACTATTGGGGTATTTGATGCTGTTGTAGGAGACATAGCTATTGTTACGAAA
CGAACAAGGATTGTGGATTTCACTCAGCCTTACATAGAATCAGGGCTTGTCGTGGTTGCTCCTGTCACAA
AGCTAAATGATACTCCGTGGGCGTTTTACGCCCTTTTACACCTCCAATGTGGGCTGTTACAGCAGCTTT
TTCCTCATCGTTGGATCAGTAATATGGATTCTTGAACATAGAATCAACGATGAGTTCCGCGGACCTCCA
AGGAAACAAATTGTTACTATTCTCTGGTTCAGCTTCTCCACGATGTTTTTCTCCCACAGAGAGAACACAG
TGAGTACACTCGGTCGTGCTGTTCTGCTCATCTGGCTATTTGTGGTACTAATCATAACATCAAGCTACAC
AGCGAGTCTTACATCGATTCTTACAGTGCAACAGCTAAACTCACCAATCAGAGGAGTAGACACACTCATC
AGCAGCAGTGGACGAGTTGGGTTTCAGGTAGGTTCTTATGCAGAAAACTACATGATTGATGAGCTTAACA
TTGCCAGATCCAGACTTGTACCACTCGGCTCTCCTAAAGAATACGCTGCAGCTCTTCAAAACGGAACTGT
TGCTGCAATTGTTGATGAGCGTCCTTACGTTGATCTCTTCCTCTCAGAATTCTGCGGATTTGCCATTAGA
GGCCAAGAATTCACCAGAAGTGGCTGGGGATTTGCATTTCCAAGAGACTCTCCATTAGCAATCGACATGT
CAACCGCGATCTTAGGTCTATCAGAAACCGGACAGCTTCAAAAGATCCATGACAAGTGGCTTTCAAGATC
TAACTGCAGTAACCTCAACGGTTCAGTGTCAGATGAAGATTCAGAACAGCTTAAACTCCGAAGCTTCTGG
GGATTATTCCTTGTGTGTGGGATCTCTTGTTTTATCGCTCTCTTCATCTACTTCTTCAAGATAGTCCGCG
ACTTCTTCCGCCACGGCAAATATGATGAAGAAGCCACAGTATCTTCACCAGAAAGTTCACGTTCTAAATC
ATTGCAGACATTTCTAGCTTATTTTGATGAAAAAGAAGACGAATCCAAGAGAAGGATGAAGCGTAAACGA
AACGATGATCTTTCTTTAAAGCCTTCTAGACCAATATGACAGATCCATCAAGACTCAAGCATGAAAGATG
AAGAAATGCAGACACACATCCTCATACTTATATAGTAGAATGCAGATTTTGATTTTAACTGTACTTCAAG
AATAATAAGCCTTGAAGAATACGGAACATTTTTTAACCAAAGAAAGTGAAGCATAAACTTGTAAGACAAA
GCTATATCATACATAGTTCTTAAAAAAAAACAATTACTTGGTATCCTTTTTTTTTTTTTTTTTTTT
(SEQ ID NO: 2)
>gi|13160471|gb|AAK13248.1| AF159498_1 putative glutamate receptor like-protein [Arabidopsis thaliana]
MFWVLVLLSFIVLIGDGMISEGAGLRPRYVDVGAIFSLGTLQGEVTNIAMKAAEEDVNSDPSFLGGSKLR
ITTYDAKRNGFLTIMGALQFMETDAVAIIGPQTSIMAHVLSHLANELSVPMLSFTALDPSLSALQFPFFV
QTAPSDLFLMRAIAEMISYYGWSEVIALYNDDDNSRNGITALGDELEGRRCKISYKAVLPLDVVITSPRE
IINELVKIQGMESRVIIVNTFPKTGKKIFEEAQKLGMMEKGYVWIATTWLTSLLDSVNPLPAKTAESLRG
VLTLRIHTPNSKKKKDFVARWNKLSNGTVGLNVYGLYAYDTVWIIARAVKRLLDSRANISFSSDPKLTSM
KGGGSLNLGALSIFDQGSQFLDYIVNTNMTGVTGQIQFLPDRSMIQPSYDIINVVDDGFRQIGYWSNHSG
LSIIPPESLYKKLSNRSSSNQHLNNVTWPGGTSETPRGWVFPNNGRRLRIGVPDRASFKEFVSRLDGSNK
VQGYAIDVFEAAVKLISYPVPHEFVLFGDGLKNPNFNEFVNNVTIGVFDAVVGDIAIVTKRTRIVDFTQP
YIESGLVVVAPVTKLNDTPWAFLRPFTPPMWAVTAAFFLIVGSVIWILEHRINDEFRGPPRKQIVTILWF
SFSTMFFSHRENTVSTLGRAVLLIWLFVVLIITSSYTASLTSILTVQQLNSPIRGVDTLISSSGRVGFQV
GSYAENYMIDELNIARSRLVPLGSPKEYAAALQNGTVAAIVDERPYVDLFLSEFCGFAIRGQEFTRSGWG
FAFPRDSPLAIDMSTAILGLSETGQLQKIHDKWLSRSNCSNLNGSVSDEDSEQLKLRSFWGLFLVCGISC
FIALFIYFFKIVRDFFRHGKYDEEATVSSPESSRSKSLQTFLAYFDEKEDESKRRMKRKRNDDLSLKPSR PI
(SEQ ID NO: 4)

FIG. 15

REPRESSION OF ATGLR3.2 INCREASES PLANT BIOMASS

PRIORITY CLAIM

This application claims benefit under 119(e) to U.S. provisional 60/820,763, filed Jul. 28, 2006.

STATEMENT OF GOVERNMENT INTEREST

There is no government interest in this invention.

FIELD OF THE INVENTION

The present invention relates to methods that may be used to improve or modify plant Nitrogen (N) sensing, absorption, assimilation, root growth, stomatal conductance, N use efficiency, carbon (C) and N metabolism, plant biomass production and seed yield. More specifically, this invention is related to the glutamate receptors (GLRs) and their role(s) in N sensing, assimilation, regulation of growth, development, and yield.

BACKGROUND OF THE INVENTION

In the central nervous system (CNS) the transmission of stimuli takes place by the interaction of a neurotransmitter, which is sent out by a neuron, with a neuroreceptor. L-glutamic acid, the most commonly occurring neurotransmitter in the CNS, plays a critical role in a large number of physiological processes. The glutamate-dependent stimulus receptors are divided into two main groups. The first main group forms ligand-controlled ion channels, ionotropic glutamate receptors (iGLR). The metabotropic glutamate receptors (mGluR) form the second main group and, furthermore, belong to the family of G-protein-coupled receptors.

Glutamate receptors are involved in neuronal synapses in mammals and other animals, controlling functions such as learning and memory. Recent genomic sequencing and Expressed Sequence Tag analyses demonstrate that plants also possess orthologues of these receptors (Lam et al. 1998. Nature 396: 125-126). Furthermore an iGLR like receptor has also been reported in Cyanobacterium *Synechosystis* PCC 6803 (Chen et al. 1999. Nature 402:817) indicating that the putative GLRs are involved in well conserved sensing processes that has evolved into neuronal signaling in higher animals.

Based on ligand selectivity and ion conductance properties, mammalian iGLRs can be classified in to multiple classes,—amino-3-hydroxy-5-methyl-4-isoxazole propionic acid (AMPA)—kainite (KA), N-methyl-D-aspartate (NMDA) and Delta receptors (Sprengel and Seeburg, Handbook of receptors and channels: Ligand and voltage gated ion channels. CRC Press. Pp. 213-263, 1995).

At present, eight different members of mGluR are known and of these some even have sub-types. On the basis of structural parameters, the different influences on the synthesis of secondary metabolites and the different affinity to low-molecular weight chemical compounds, these eight receptors can be subdivided into three sub-groups: mGluR1 and mGluR5 belong to group I, mGluR2 and mGluR3 belong to group II and mGluR4, mGluR6, mGluR7 and mGluR8 belong to group III.

In *Arabidopsis thaliana* there are twenty of these receptor genes called glutamate receptors, that have been characterized by expression, and phylogenetic analyses (Chiu et al. 2002. Mol. Biol. Evol. 19:1066). Physiological analyses show that these receptors are involved in the regulation of C/N metabolism, calcium homeostasis, and stress responses (Kang and Turano. 2003. PNAS. 100:6872; Kim et al. 2001. Plant Cell Physiol. 42:74; Meyerhoff et al. 2005. Planta. 222:418).

Cell growth (accumulation of mass) is an extensively coordinated process that is regulated in both time and space. When nutrients and other appropriate growth stimuli are present, cells up regulate macromolecular synthesis and thereby increase in size and mass. Conversely, cells respond to nutrient limitation or other types of stress by restraining macromolecular synthesis and enhancing turnover of excess mass.

The target of rapamycin (TOR) is a conserved Ser/Thr kinase that regulates cell growth and metabolism in response to environmental cues. Every eukaryotic genome examined including yeasts, algae, slime mold, plants, worms, flies and mammals contain a TOR gene. Eukaryote TORs are large proteins (~280 kDa) that share 40%-60% identity in their primary sequence and belong to a group of kinases known as the phosphatidylinositol kinase-related kinase (PIKK) family.

When growth conditions are favorable, TOR is active and yeast cells maintain a robust rate of ribosome biogenesis, translation initiation, and nutrient import. However, rapidly growing yeast cells treated with rapamycin, starved for nitrogen, or depleted of both TOR1 and TOR2 dramatically downregulate general protein synthesis, upregulate macroautophagy (the random sequestration and delivery of cytoplasm to the lysosome/vacuole), and activate several stress-responsive transcription factors. Growth factors, nutrients esp. amino acids, energy and stress regulate TOR pathway. However how amino acid levels are signaled to TOR is not fully understood. (Wullschleger et al. Cell. 2006. 124, 471).

Organisms modulate their growth according to nutrient availability. Although individual cells in multicellular organism including animal may respond directly to nutrient levels growth of entire organism needs to be co-coordinated. In *Drosophila* the coordination of organismal growth from the fat body is well studied. This involves TOR signaling in the fat body and a remote inhibition of organismal growth via local repression of PI3 kinase signaling in peripheral tissues (Colombani et al. Cell. 2003, 114, 739) In the rat, mammalian TOR (mTOR) in hypothalamus regulates food intake based on the level of amino acids (Cota et al. Science 2006. 312, 927).

N is an important macronutrient in modern agriculture with significant economic and ecological impact (Nanjing declaration on N management www.initrogen.org/nanjing_declaration.0.html). The yield of crop plants is directly related to the level of N applied. Modern crop production systems exploit plant breeding methods to develop high yielding, N responsive crop plants with increases in harvest index and biomass production (Hirel et al. 2001. Pl. Phyiol. 125, 1258, Peng et al. 2000 Crop Sci. 40, 307). Genomic and physiological approaches in plant breeding are expected to provide further improvements in yield. For example, selection for improved photosynthetic rates and stomatal conductance are considered important physiological characteristics for yield improvement in wheat (Reynolds et al. 1999 Crop Sci. 39, 1611). Molecular approaches that include (i) over expression of key enzymes involved in N assimilation such as glutamine synthetase (GS) and asparagine synthetase (AS) in *Arabidopsis* and pea (U.S. Pat. No. 6,864,405), (ii) reduced expression of enzymes involved in cytokinin catabolism like an isoform of cytokinin oxidase in rice spiklets (Yanagisawa et al. Proc. Natl. Acad. Sci. USA. 2004. 101, 7833) and (iii) overexpression of transcription factor Dof1 in *Arabidopsis* (Ashikari et al. 2005. Science 309, 741) are shown to have improved biomass, N assimilation and yield. While N sensing is known to co-ordinate the up regulation of genes involved in many of the above mentioned pathways (Scheible et al. Plant Physiol. 2004. 136:2483), molecular components involved in the sensing processes remained elusive.

N is taken up by plants mostly in the form of nitrate or ammonium by specific nitrate or ammonium transporters, respectively. Upon uptake N is transformed into amino acids through the GS-GOGAT pathways (FIG. 1, G. M. Coruzzi. 2003. The *Arabidopsis* book). Plants transport N mostly as amino acids, though smaller amounts of nitrate and ammonia can be detected in the transporting vessels. There is tremendous interest in how plants sense the N status at the cellular and at whole plant level. The level of endogenous N regulates various processes including photosynthesis, major metabolic pathways, protein and DNA syntheses and growth and development (Scheible et al. Plant Physiol. 2004. 136:2483-99). Nitrate and ammonium are known to induce a set of genes that are involved in N uptake, assimilation pathways. However, inhibitors such as azaserine or methionine sulfoximine which inhibit the GS-GOGAT pathway, were shown to inhibit the nitrate induced signaling pathways (Vidamer et al. 2000 Plant Physiol. 123: 307, Kawachi et al. 2002. Physiol. Plantarum 114: 41). Plant orthologues of bacterial PII proteins, a regulator of bacterial N metabolism has been identified (U.S. Pat. Nos. 6,822,079, 6,177,275). However the role these proteins play in plant N sensing is not known. Similarly, *Arabidopsis thaliana* glutamate receptor 1.1 (AtGLR1.1) has been shown to be involved in the regulation of C and N metabolism (Kang and Turano. 2003. PNAS. 100:6872). Currently scientists do not have a clear understanding of the molecular components in N sensing in higher plants.

Currently with the available agricultural technologies the loss of applied N is estimated to be 60-70% (Raun, W R. and Johnson G V. 1999. Agronomy Journal. 91:357). Development of crop plants with improved N use efficiency has significant economic and ecological value. The yield level of crop plants is directly related to the level of N applied. Modern crop production systems exploit plant breeding methods to develop high yielding, N responsive crop plants with increased harvest index and biomass production (Hirel et al. 2001. Pl. Phyiol. 125, 1258, Peng et al. 2000 Crop Sci. 40, 307). There is a need for technology to generate, and/or select plants with improved N use efficiency, biomass and yield, and plants with improved nutritional value. These traits are of economic importance. Presently plant biologists do not have a technology that can improve N sensing and yield, and thus there is a need for technology which provides a method to develop crop plants with higher N sensing capability that result in higher biomass and yield.

SUMMARY OF THE INVENTION

Glutamate receptors of the nucleic acid sequences of SEQ ID NO: 1 and/or SEQ ID NO: 2, wherein they regulate amino acid sensing, metabolism, growth and development. Further glutamate receptor gene product is at least 20%, 30%, 40%, 50%, 60%, 70%, 80%, 90%, or 99% similar to SEQ ID NO: 1 and/or SEQ ID NO: 2.

In one preferred embodiment, the invention includes a method for developing a plant or cell line or a clone that is efficient in N use, growth and yield, comprising: obtaining and/or selecting a plant or cell line or a clone that have modified levels or efficiency of glutamate receptor(s) compared to a progenitor plant, wherein the plant demonstrates improved or modified N sensing responses. Another preferred embodiment includes a transgenic plant obtained by the above mentioned method, wherein the plant has an operable gene construct comprising a nucleic acid encoding a glutamate receptor linked to a promoter which regulates N assimilation/metabolism enzymes selected from GS, AAT, and Fd-GOGAT, and the transgenic plant exhibits one or more traits selected from: i) faster rate of growth, ii) greater fresh or dry weight at maturation, iii) greater fruit or seed yield, iv) greater total plant N content, v) greater fruit or seed N content, vi) greater free amino acid content in the whole plant, vii) greater free amino acid content in the fruit or seed, viii) greater protein content in seed or fruit, ix) greater protein content in a vegetative tissue, x) greater amount of products including one or more of oils, polymers, enzymes, antibodies, or metabolites, or xi) greater ability to resist disease or pest damage, than a progenitor plant which does not contain the gene construct, when the transgenic plant and the progenitor plant are cultivated under identical N non-limiting growth conditions.

In another preferred embodiment, a method for developing a plant that is modified in specific C and N metabolic pathways to a particular product is provided, comprising: obtaining and selecting a plant that has modified levels or efficiency of glutamate receptors compared to a progenitor plant, using to assist said selection.

A modified plant obtained by the above method is also provided, wherein the plant has an operable gene construct comprising a nucleic acid encoding a glutamate receptor linked to a promoter which regulates N assimilation/metabolism enzymes selected from GS, AAT, and Fd-GOGAT, and the transgenic plant exhibits one or more traits: i) faster rate of growth, ii) greater fresh or dry weight at maturation, iii) greater fruit or seed yield, iv) greater total plant N content, v) greater fruit or seed N content, vi) greater free amino acid content in the whole plant, vii) greater free amino acid content in the fruit or seed, viii) greater protein content in seed or fruit, ix) greater protein content in a vegetative tissue, x) greater amount of products including one or more of oils, polymers, enzymes, antibodies, or metabolites, or xi) greater ability to resist disease or pest damage, than a progenitor plant which does not contain the gene construct, when the transgenic plant and the progenitor plant are cultivated under identical N non-limiting growth conditions.

In yet another preferred method, there is provided a method for developing a plant that is efficient in nutrient uptake, comprising: obtaining and selecting a plant that has modified levels of glutamate receptors compared to a progenitor plant, using methodologies to assist said selection, wherein the plant demonstrates improved N sensing responses, and wherein nutrient uptake is improved compared to the progenitor plant.

A transgenic plant obtained by the above method is provided, wherein the plant has an operable gene construct comprising a nucleic acid encoding a glutamate receptor linked to a promoter which regulates N assimilation/metabolism enzymes selected from GS, AAT, and Fd-GOGAT, and the transgenic plant exhibits one or more traits selected from: i) faster rate of growth, ii) greater fresh or dry weight at maturation, iii) greater fruit or seed yield, iv) greater total plant N content, v) greater fruit or seed N content, vi) greater free amino acid content in the whole plant, vii) greater free amino acid content in the fruit or seed, viii) greater protein content in seed or fruit, ix) greater protein content in a vegetative tissue, x) greater amount of products including one or more of oils, polymers, enzymes, antibodies, or metabolites, or xi) greater ability to resist disease or pest damage, than a progenitor plant which does not contain the gene construct, when the transgenic plant and the progenitor plant are cultivated under identical N non-limiting growth conditions.

A further preferred embodiment includes a method for developing plants that are efficient in water use, comprising: obtaining and/or selecting plants that have modified levels or efficiency of glutamate receptor compared to a progenitor plant, wherein the plant demonstrates reduced N sensing responses, and wherein water use is improved compared to the progenitor plant.

A modified plant obtained by the above method is provided, wherein the plant has an operable gene construct comprising a nucleic acid encoding a glutamate receptor linked to a promoter which regulates N assimilation/metabolism enzymes selected from GS, AAT, and Fd-GOGAT, and the plant exhibits greater efficiency in water use, than a progenitor plant when the transgenic/modified plant and the progenitor plant are cultivated under identical N non-limiting growth conditions.

In the above transgenic plant, water efficiency comprises altered stomatal conductance and reduced transpirational loss.

A modified plant wherein the plant has operable gene construct with an antisense expression cassette or a sense suppression or a knock out or any other methods of down regulating the expression resulting in improved N sensing, assimilation, biomass production, stomatal conductance and water use.

A transgenic plant having a gene construct comprising a gene encoding a glutamate receptor operably linked to a plant promoter so that the glutamate receptor is overexpressed in the transgenic plant, and the transgenic plant exhibits:
i) faster rate of growth,
ii) greater fresh or dry weight at maturation,
iii) greater fruit or seed yield,
iv) greater total plant nitrogen content,
v) greater fruit or seed nitrogen content,
vi) greater free amino acid content in the whole plant,
vii) greater free amino acid content in the fruit or seed,
viii) greater protein content in seed or fruit, or
ix) greater protein content in a vegetative tissue,
than a progenitor plant which does not contain the gene construct, when the transgenic plant and the progenitor plant are cultivated under identical growth conditions, wherein the glutamate receptor gene product is substantially identical to AtGLR3.2 polypeptide SEQ ID NO: 4).

The transgenic plant, wherein the plant promoter is a strong, constitutively expressed plant promoter.

The transgenic plant, wherein the glutamate receptor gene product is at least 99% identical to AtGLR3.2 polypeptide (SEQ ID NO: 4).

A seed of the transgenic plant, wherein the seed has the gene construct.

A progeny, clone, cell line or cell of the transgenic plant wherein said progeny, clone, cell line or cell has the gene construct.

BRIEF DESCRIPTION OF THE FIGURES

FIG. 3 is in five parts, the first three are photographs and the last two are bar charts.

FIG. 3 shows the differences in LR elongation between A, line CC7 (antiAtGLR1.1), B, ecotype WS (WT) and C, line B11 (antiAtGLR3.2) plants. The black bar represents a 1 cm scale. The plants were grown in 100 µM nitrate on Petri dishes. D. Quantification of LR lengths for 15 plants from WT, antiAtGLR3.2 lines A1b and B11 demonstrate that antiAtGLR3.2 plants have a 60% increase in the total LR length compared with WT. E. Quantification of total LR length between WT and antiAtGLR1.1 line CC7 demonstrated that antiAtGLR1.1 plants have 42% less LR length compared with the WT. The seedlings were grown for 12-14 days on 100 µM nitrate medium as per Zhang, H. and Forde, B. G. 1998 Science 279:407-409. The asterisk indicates significant difference compared to the control, ($P<0.05$ in a ttest).

FIG. 4 shows the LR elongation response is specific and localized, which is "gold-standard" for the N-response. The antiAtGLR3.2 plants were grown in a segmented plate with 100 µM KNO3 (A) or 100 µM KCl. (B), all the three segments contained 10 µM KNO3. Note, elongation of LR in KNO3 zone (a) versus KCl, control, (B). Analysis of the middle segment demonstrated significant difference in the LR length in the KNO3-treated roots ($n=3$, $P<0.05$ in at test).

FIG. 14 is SEQ ID No. 1 (mRNA) and SEQ ID No. 3 (polypeptide) of AtGLR1.1.

FIG. 15 is SEQ ID No. 2 (mRNA) and SEQ ID No. 4 (polypeptide) of AtGLR3.2.

DETAILED DESCRIPTION

Definitions

Figure 1:
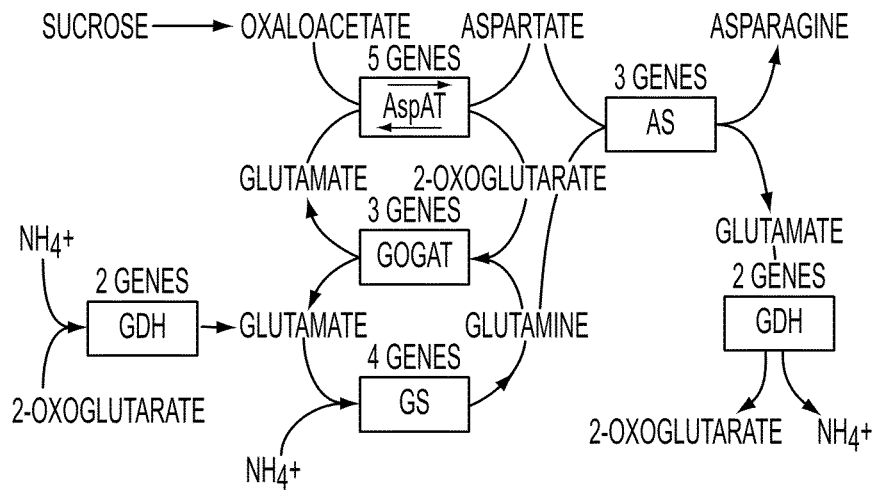
FIG. 1 is a drawing of a metabolic cycle and shows the GS-GOGAT pathway and N uptake and conversion to amino acids in plants. GDH—Glutamate dehydrogenase, AspAT—Aspartate amino transferase, AS—Asparagine synthetase, GS—Glutamine synthetase, GOGATGlutamate synthase.

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. Examples of means by which this can be accomplished are described below, and include *Agrobacterium*-mediated transformation, biolistic methods, electroporation, in planta techniques, and the like. In contrast, a polynucleotide sequence or polypeptide sequence "endogenous" to a plant refers to a native sequence which is introduced into the plant, or a predecessor generation of the plant, by a sexual cross and that is not a transgenic or other synthetic sequence. Of course, standard genetic manipulations of plants (e.g., by crossing non-transgenic plants).

While all of the gene products described above were originally derived from *Arabidopsis*, those of skill in the art will recognize that orthologous gene products from a variety of species, as well as variants substantially identical to such gene products, are known or can be isolated using routine molecular biology techniques.

An "expression cassette" refers to a nucleic acid construct, which when introduced into a host cell, results in transcription and/or translation of an RNA or polypeptide, respectively. Antisense or sense constructs that are not or cannot be translated are expressly included by this definition. The phrase "host cell, cell lines or clones" refers to a cell from any organism. Preferred host cells/clones are derived from plants, bacteria, yeast, fungi, insects or other animals. Methods for introducing polynucleotide sequences into various types of host cells are well known in the art.

The "biological activity of a polypeptide" refers to any molecular activity or phenotype that is caused by the polypeptide. The "activity of AtGLR1.1", "activity of AtGLR3.2", "activity of a polypeptide related to SEQ ID NO: 3" or the "activity of a polypeptide related to SEQ ID NO: 4" includes the ability to modulate cellular metabolism and development, by their ion channel activity and/or influencing downstream signaling pathways such as by protein-protein interaction, the effect of these pathways such as (1) nutrient sensing, such as N and phosphate, (2) N assimilation, (3) regulation of C and N metabolism (4) regulation of stomatal conductance in higher plants, (5) regulation of growth and development, (6) regulation of biomass production and yield, (7) Regulation of biotic and abiotic stress tolerance.

In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived. As explained below, these substantially identical variants are specifically covered by the terms glutamate receptor nucleic acid, AtGLR1.1 nucleic acid, and AtGLR3.2 nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms glutamate receptor nucleic acid, AtGLR3.2 nucleic acid, and AtGLR1.1 nucleic acid". In addition, the term specifically includes those sequences substantially identical (determined as described below) with a AtGLR1.1 or AtGLR3.2 polynucleotide sequences disclosed here and that encode polypeptides that are either mutants of wild type AtGLR1.1 or AtGLR3.2 polypeptides or retain the biological activity of the AtGLR1.1 or AtGLR3.2 polypeptide (e.g., resulting from conservative substitutions of amino acids in the AtGLR1.1 or AtGLR3.2 polypeptide).

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

The term "substantial identity" of polynucleotide sequences means that a polynucleotide comprises a sequence that has at least 20% sequence identity. Alternatively, percent identity can be any integer from 20% to 100%. More preferred embodiments include at least: 25%, 30%, 35%, 40%, 45%, 50%, 55%, 60%, 65%, 70%, 75%, 80%, 85%, 90%, 95%, or 99% compared to a reference sequence using the programs described herein; preferably BLAST using standard parameters, as described below. Accordingly, glutamate receptor sequences of the invention include nucleic acid sequences that have substantial identity to SEQ ID NO:1, or SEQ ID NO:2.

Glutamate receptor polypeptide sequences of the invention include polypeptide sequences having substantial identity to SEQ ID NO: 3 or SEQ ID NO: 4. One of skill will recognize that these values can be appropriately adjusted to determine corresponding identity of proteins encoded by two nucleotide sequences by taking into account codon degeneracy, amino acid similarity, reading frame positioning and the like. "Substantial identity" of amino acid sequences for these purposes normally means sequence identity of at least 40%. Percent identity can be determined by comparison to a reference sequence using the programs described herein; preferably BLAST using standard parameters, as described below. This definition also refers to the complement of a test sequence, when the test sequence has substantial identity to a reference sequence. Preferred percent identity of polypeptides can be any integer from 20% to 100%. More preferred embodiments include at least 30%, 40%, 50%, 55%, 60%, 65%, 70%, 75%, 80%, 85%, 90%, 95%, or 99%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUR PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih go-v/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength. (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, highly stringent conditions are selected to be about 5-10.degree. C. lower than the thermal melting point (T.sub.m) for the specific sequence at a defined ionic strength pH. Low stringency conditions are generally selected to be about 15-30.degree. C. below the T.sub.m. The T.sub.m is the temperature (under defined ionic strength, pH, and nucleic concentration) at which 50% of the probes complementary to the target hybridize to the target sequence at equilibrium (as the target sequences are present in excess, at T.sub.m, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30.degree. C. for short probes (e.g., 10 to 50 nucleotides) and at least about 55.degree. C., 60.degree. C. and sometimes 65.degree. C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising ionotropic glutamate receptor nucleic acids such as AtGLR1.1 or AtGLR3.2 nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37.degree. C., and at least one wash in 0.2.times.SSC at a temperature of at least about 50.degree. C., usually about 55.degree. C. to about 60.degree. C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

For marker-assisted selection, it is preferred that the marker is a genetic marker (eg. a gene or allele), or a physical marker (eg. leaf hairiness or pod shape), or a molecular marker such as, for example, a restriction fragment length polymorphism (RFLP), a restriction (RAPD), amplified fragment length polymorphism (AFLP), or a short sequence repeat (SSR) such as a microsatellite, or single nucleotide polymorphism (SNP). It is also within the scope of the invention to utilize any hybridization probe or amplification primer comprising at least about 10 nucleotides in length derived from a chromosome region that is linked in the genome of a plant to an ionotropic glutamate receptor locus, as a marker to select plants. Those skilled in the art will readily be able to determine such probes or primers based upon the disclosure herein, particularly for those plant genomes which may have sufficient chromosome sequence in the region of interest in the genome The term "plant" includes whole plants, and plant organs, and progeny of same. Plant organs comprise, e.g., shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like). The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

Plants that can be made to have enhanced or modified N sensing by practice of the present invention include, but are not limited to, *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, cilantro, citrus, clementines, coffee, corn, cotton, cucumber, Douglas fir, eggplant, endive, escarole, eucalyptus, fennel, figs, forest trees, gourd, grape, grapefruit, honey dew, jicama, kiwifruit, lettuce, leeks, lemon, lime, Loblolly pine, maize, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini.

The results described here demonstrate that an orthologue of the animal glutamate receptor, AtGLRs function in N sensing and they modulate N absorption, assimilation, growth, development and yield in plants.

Plants that are modified to have reduced levels of AtGLR3.2 (antiAtGLR3.2) using antisense methodologies demonstrate improved N sensing responses. Conversely, plants that are modified to have reduced levels of AtGLR1.1 (antiAtGLR1.1) using antisense methodologies demonstrate reduced N sensing responses. The antiAtGLR3.2 plants demonstrate increased levels of PR and LR growth compared to WT, while antiAtGLR1.1 demonstrate reduced levels of LR growth (FIG. 3).

Figure 12:
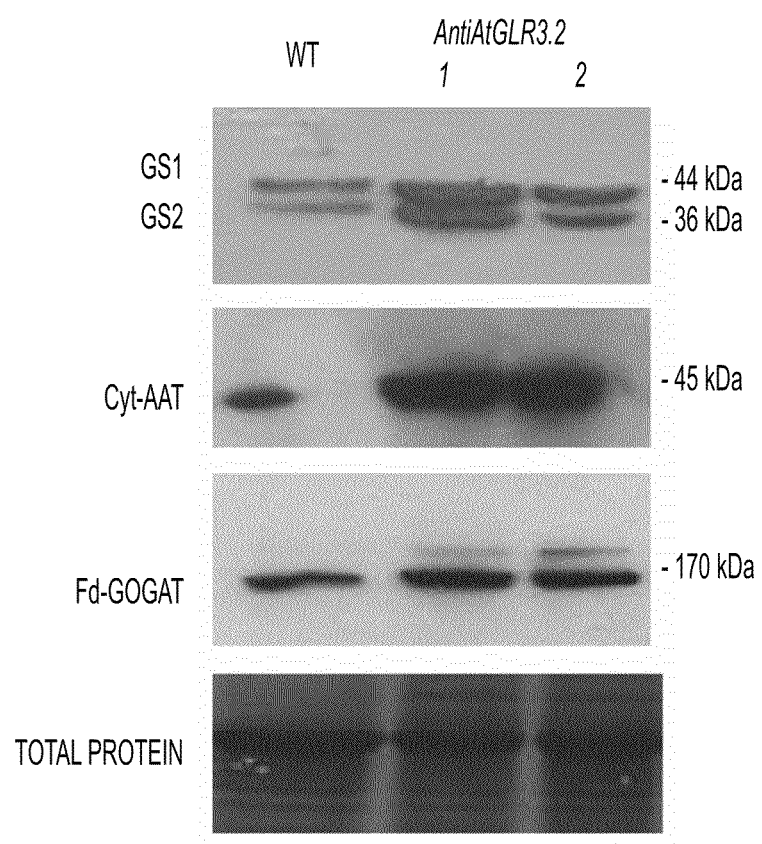
FIG. 12 is an immunoblot photomicrograph and shows immunoblot analyses of antiAtGLR3.2 lines versus WT. AntiAtGLR3.2 plants have increased levels of GS, Fd-GOGAT and cytsolicAAT when compared with WT. Equal loading of the protein was verified by protein staining with Coomassie brilliant blue.
Figure 13A:
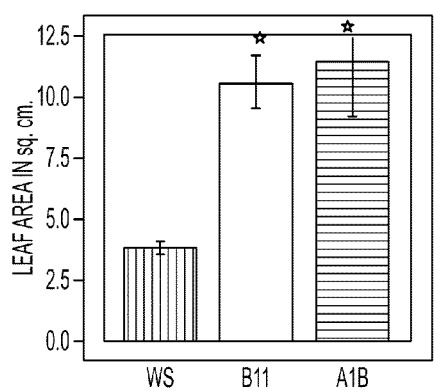
FIG. 13 is a bar chart (A) and three photos (B) which show that the antiAtGLR3.2 plants have a 289% increase in biomass production when compared with wild type (WT). Total leaf area was measured in four-week-old seedling (N=6, P<0.05 in a test).
Figure 13B:
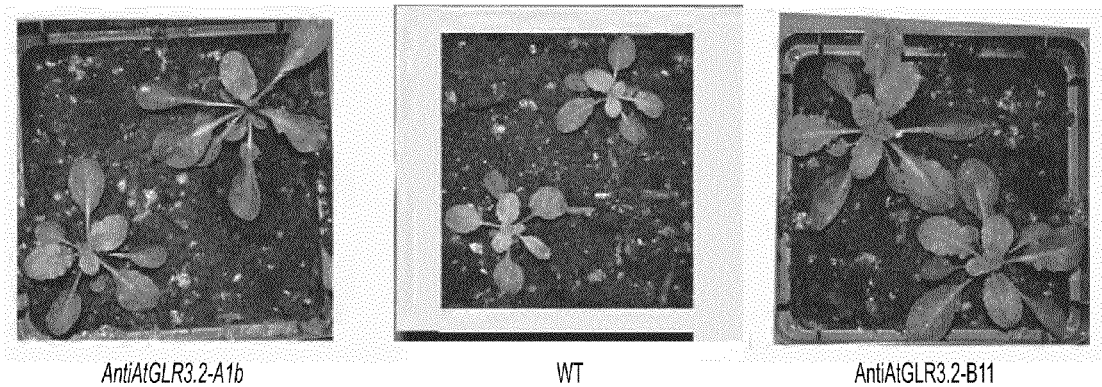

The antiAtGLR3.2 plants have higher levels of N assimilatory enzyme GS, AAT and Fd-GOGAT (FIG. 12). The anti-AtGLR1.1 plants are already known to have reduced levels of GS, AAT2 and Fd.-GOGAT. The fact that these two independent AtGLR lines have opposing effects on N sensing and N assimilatory enzymes suggests that AtGLRs can both positively or negatively control these processes in higher plants. Over expression of GS or other key enzymes involved in N assimilation are known to have increased N assimilation, increased levels of amino acid, vegetative and seed proteins, increase in growth and development, and seed yield (U.S. Pat. No. 6,864,405). The improved levels of N assimilation enzymes in antiAtGLR3.2 support the hypothesis that the AtGLRs as a N sensing system regulate N assimilation based on the levels of N sensed. Thus these findings clearly demonstrate that AtGLRs form an important component of N sensing system. The fact that antiAtGLR3.2 lines have increased levels of N assimilation enzymes suggest that these plants will also have increase in levels of amino acids, proteins and yield. By optimizing the levels of N sensing, using AtGLRs, it is possible to improve the efficiency of biomass production and yield levels. The antiAtGLR3.2 plants demonstrated 289% improved biomass levels compared to the wild type.

Figure 10A:
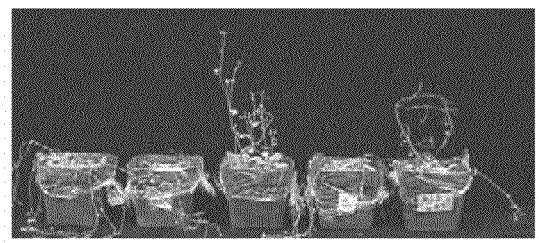
FIG. 10 is a photograph (A) and shows antiAtGLR3.2 plants display susceptibility to drought stress compared to WT. Four different lines of antiAtGLR3.2 were screened. The graph (B) shows that these plants have higher transpiration rates when compared with WT plants. Quantification of levels of transpiration during a 72 hour period is presented as a graph. The antiAtGLR.2 plants had 82% increase in the levels of transpiration.
Figure 10B:
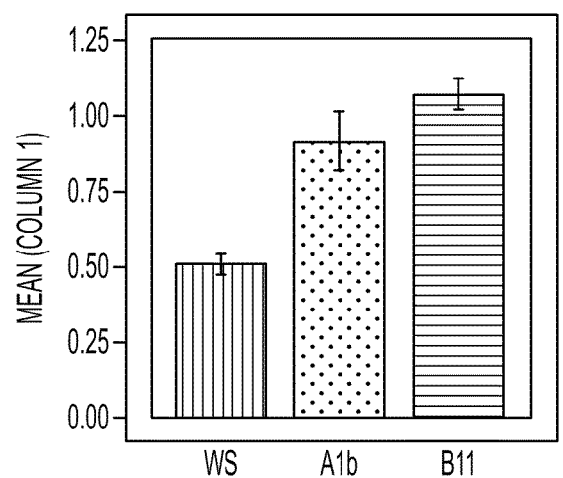

AtGLRs also modulate stomatal conductance based on the levels of N sensed, antiAtGLR3.2 plants with improved N sensing demonstrate increased water loss in drought experiment (FIG. 10). The antiAtGLR1.1 plants with reduced N sensing, are known to have reduced transpirational loss. These modifications demonstrate potential mechanisms to develop plants that are efficient in water use.

Improvements in N sensing also result in improved transpiration rate. It is a common knowledge among plant breeders that high yielding varieties have higher transpiration rates. The antiAtGLR3.2 plants which have improved N sensing also have increased transpiration rates. It had also been pointed out that improvements in growth rate also result in improvement in transpiration rate. Thus, though antiAtGLR3.2 plants have higher transpirational rate, they may be more efficient when we compare transpiration for unit biomass production. The knowledge on the role of AtGLRs in regulating the transpiration also offers an opportunity to improve or optimize the transpiration rate.

Figure 2:
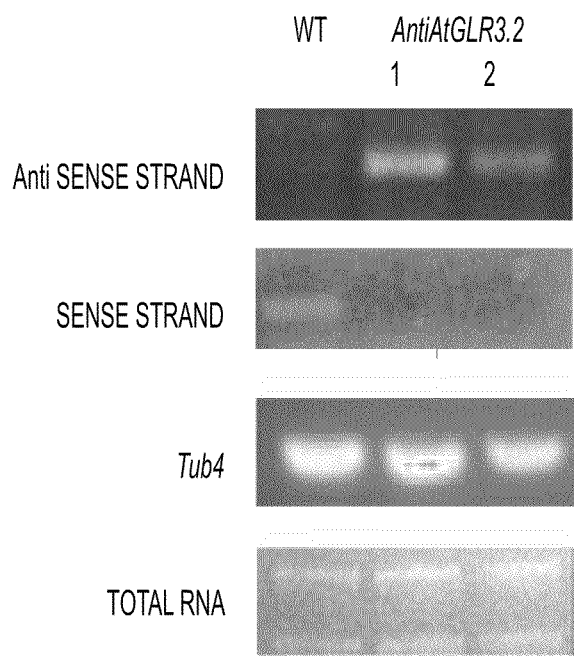
FIG. 2 is an image of RT-PCR analysis and shows the presence of the gene construct expressing the antisense AtGLR3.2 (antisense) and the down regulation of the endogenous AtGLR3.2 (sense AtGLR3.2) transcripts, with Tub4 and total RNA used as controls. The presence of the antisense and sense AtGLR3.2 transcripts were evaluated by RT-PCR protocol. Tub4 and total RNA were used as controls to ensure equal concentration.
Figure 11:
FIG. 11 is a photograph and shows antiAtGLR3.2 plants produce higher biomass in the preliminary studies when compared to Col 0.

Using lateral root (LR) elongation assay (Zhang, H. and Forde, B. G. 1998. Science. 279:407-409), which has been shown to be a physiological response assay for N sensing, N sensing was tested in antisense AtGLR1.1 (antiAtGLR1.1) (Kang and Turano. 2003. PNAS. 100:6872) and antisense AtGLR.3.2 (antiAtGLR3.2) plants (FIG. 2). The present invention describes the function for AtGLRs in N sensing, absorption (FIG. 3, Forde, B G. 2002. Annu. Rev. Plant Biol. 53:203), assimilation (FIG. 12), plant growth and development (FIG. 11, 13). These claims were validated with pharmacological (FIG. 6-9), physiological (FIG. 10, 11, 13) and immunobot analyses of N assimilatory enzymes (FIG. 12).

Using antiAtGLR1.1 and antiAtGLR3.2 lines, it is demonstrated that these plants have modified sensing response to different levels of nitrate. The antiAtGLR1.1 plants, which were shown to have reduced levels of AtGLR1.1 receptors (Kang and Turano. 2003. PNAS. 100:6872), are demonstrated here to have reduced levels of lateral root elongation compared with wild type (FIG. 3). When grown on 100 μM nitrate nutrient plates (Zhang, H. and Forde, B. G. 1998. Science. 279:407), the antiAtGLR1.1 line CC7 had 42% less total lateral root length compared to the WT. The antiAtGLR1.1 plants have reduced levels of major N absorption and assimilation transcripts/proteins, and reduced levels of transpiration (Kang and Turano, 2003. PNAS. 100:6872, Kang et al. 2004. Plant Cell Physiol. 45: 1380). These findings demonstrate that while AtGLR1.1 senses N and control growth and development, reduced levels of AtGLR1.1 as in antiAtGLR1.1 resulted in reduced levels of N sensing and reduced LR growth. The reduced N sensing also resulted in reduced levels of N absorption and assimilation enzymes, and reduced transpiration as described previously (Kang and Turano. 2003. PNAS. 100:6872).

Figures 4A, 4B:
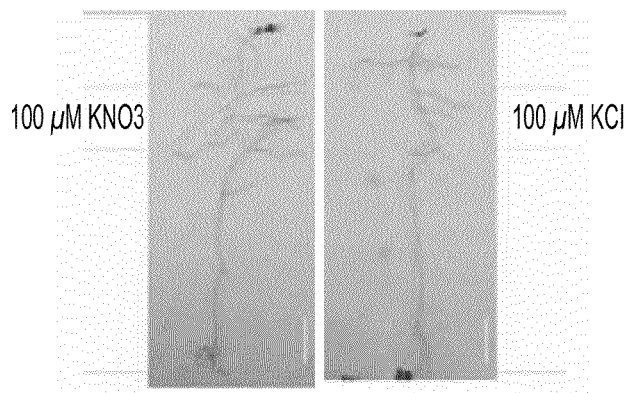
FIG. 4 is in three parts, the first two are photographs and the last is a bar graph.
Figure 4C:
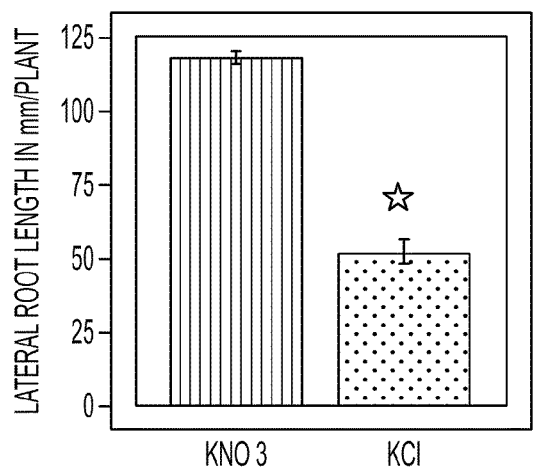
Figure 5:
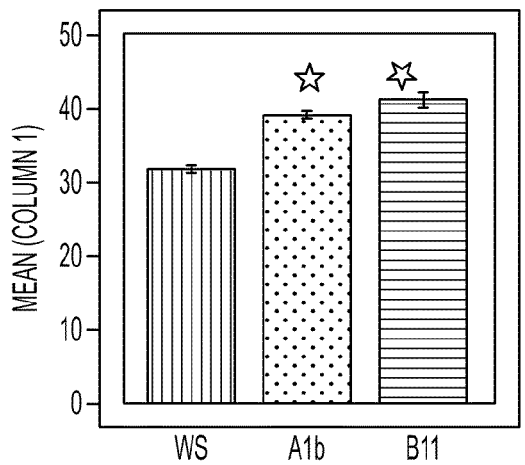
FIG. 5 is a bar graph and shows antiAtGLR3.2 plants have 21% increased primary root length compared to WT. Nine plants were grown on 100 µM nitrate medium as per Zhang et al. 1999. The asterisk indicates significant difference compared to the control, ($n=9$, $P<0.05$ in at test).

Similar assays were performed with antiAtGLR3.2 plants. The antiAtGLR3.2 lines A1b and B11 which have reduced levels of the endogenous AtGLR3.2 transcript (FIG. 2) compared with the WT. The antiAtGLR3.2 plants demonstrated a 600% increase in their total lateral root elongation compared with the WT (FIG. 3). Furthermore, analyses of antiAtGLR3.2 plants demonstrated that the LR elongation response is localized (FIG. 4). The localized nature of root elongation suggests that increased LR elongation is a specific response to a stimulatory signal, N and not an improved growth response nor a result of hormonal imbalance. The localized nature of the response is a hall mark of a signaling response and is well established in scientific literature (Zhang and Forde. 1998. Science. 279:407). This hypothesis that antiAtGLR3.2 plants have improved N sensing is supported by the analysis of major N regulated processes: the antiAtGLR3.2 plants also have increased levels of major N assimilation enzymes (FIG. 12), higher rates of transpiration (FIG. 10) and biomass production (FIG. 11, 13). Thus antiAtGLR3.2 plants have significantly improved (60%) N sensing compared with the WT, as quantified by the LR elongation assay. This data shows that AtGLR3.2 function in a novel way to regulate or modulate the N sensing negatively. Negative regulators in signal transduction systems can play a valuable role in modulating the signal (Bhalla et al. 2002. Science 297:1018-1023). They potentially improve the robustness of response. For example, by discounting the N sensed at the cellular level to a certain degree, organisms can grow on a conservative trajectory for a longer time, potentially tide over regimes of lower nutrient availability. This may have ecological and evolutionary advantages as plants grow in the wild with uneven and uncertain access to major nutrients. The antiAtGLR3.2 plants also have 21% increase in primary root (PR) growth when compared with WT (FIG. 4). Thus AtGLRs form a N sensing network consisting of positive and negative regulators. AtGLR1.1 acts as a positive regulator sensing the levels of N. AtGLR3.2 forms a negative modulator of N sensing. Integration of these signals regulates the levels of N sensing, metabolism, growth, development and yield as demonstrated here.

Figure 6A:
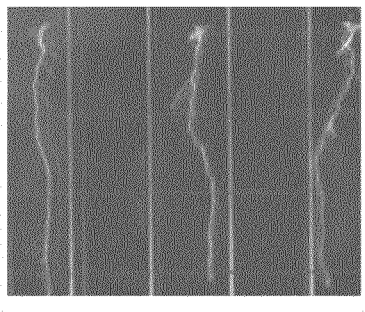
FIG. 6 is a two part photograph and shows DNQX at 400 µM can reversibly and temporarily inhibit LR growth and elongation. A. Control, B. DNQX treated. Note the lack of LR in DNQX-treated seedlings (b) versus LR in DMSO control. Both plates contained 10 µM KNO3. DNQX is an inhibitor (antagonist) of animal iGLRs and plant GLRs. The lateral root in the DMSO control is indicated by an arrow.
Figure 6B:
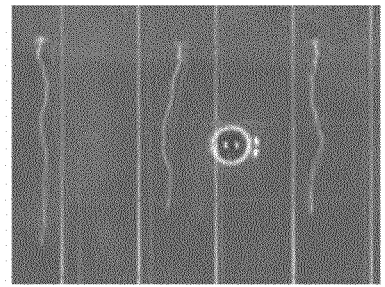
Figure 7A:
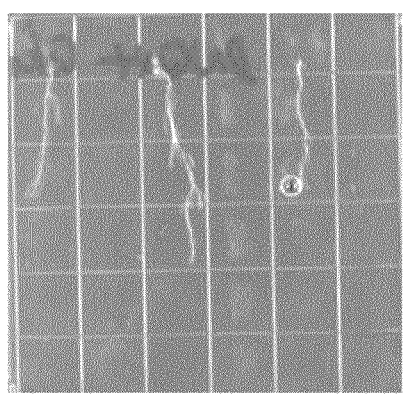
FIG. 7 is a two part photograph and shows DNQX inhibition can be reversed by co-incubation with A. 10 mM Glu but not B. 10 mM KNO3. Note glutamate is the natural binding chemical (ligand) to animal iGLRS and puataive ligand for plant GLRs.
Figure 7B:
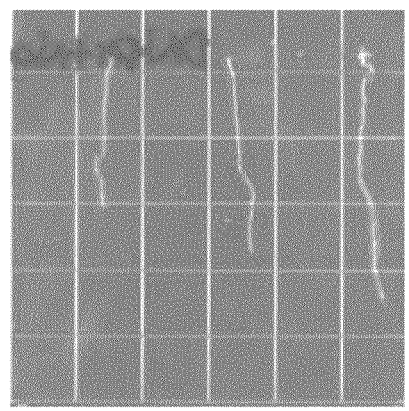
Figure 8A:
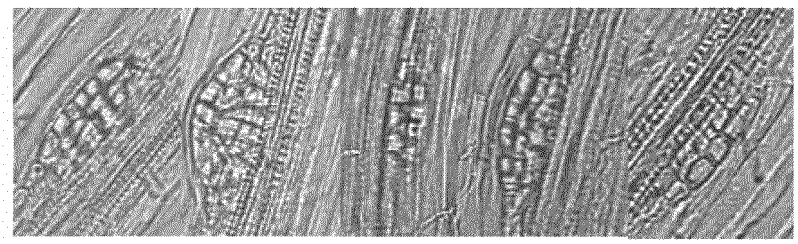
FIG. 8 is a two part photomicrograph and shows A. 400 µM of DNQX inhibits number of LRP formed and their elongation. B. DMSO control had fully emerged LR and more LRPs Arrows indicate an LRP that is inhibited, (A) or a fully emerged LR, (B).
Figure 8B:
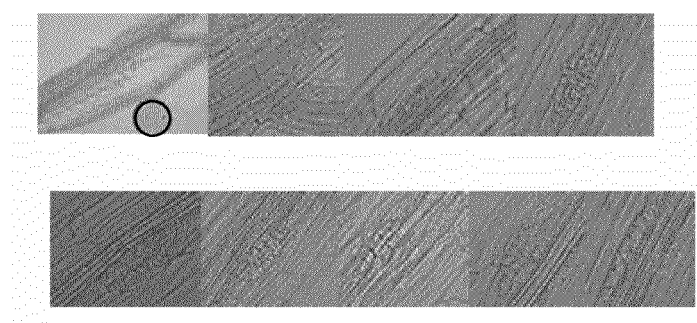
Figure 9A:
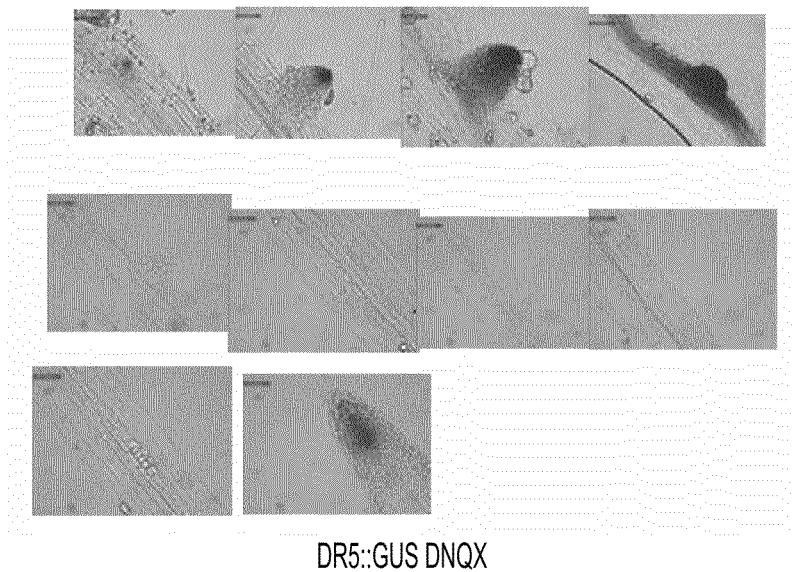
FIG. 9 is a two part serial of photographs and shows the effect of DNQX on auxin responsive reporter DR5::GUS expression in PR and LR apex. DNQX treatment results in hyper accumulation of auxins. DR5::GUS reporter was grown for 10 days and subjected to histochemical GUS staining for 10 hrs. The development of blue color indicates the detection of the presence of auxins that function in the regulation and formation of lateral roots
Figure 9B:
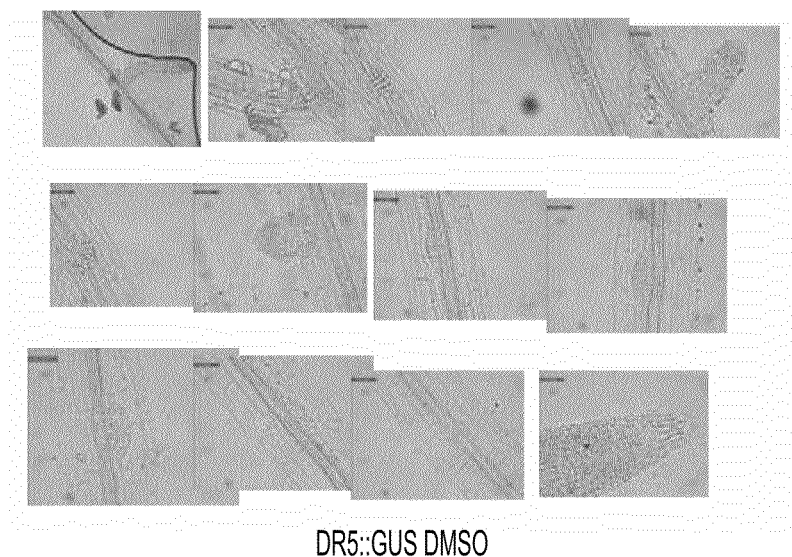

The genetic and physiological analyses described above were complemented with pharmacological studies where the functions of AtGLRs were inhibited with iGLR specific inhibitors/antagonists. Analyzes performed with iGLR antagonist, 6,7 dinitroquinoxaline-2-3-[1H,4H]-dione (DNQX) at 400 μM demonstrate that the antagonist inhibit PR and LR elongation (FIG. 6). DNQX mediated PR and LR inhibition was restored to normal growth when seedlings were transferred to a media without DNQX. DNQX mediated inhibition was restored to normal growth by coincubation with 10 mM L-glutamate (L-Glu) but not by 10 mM nitrate (FIG. 7). L-Glu is the bioactive ligand for iGLRs. The iGLR antagonist DNQX has been shown to block L-Glu induced ion channel activity in plants (Mayerhoff et al. 2005. Planta. 222:418). Microscopic analyses revealed that while DNQX reduced the number of LR primordia initiation, further elongation of primordia is inhibited in antiAtGLR1.1 plants compared to DMSO control (FIG. 8). Thus the inhibitors of AtGLRs can block LR elongation drastically and specifically. Furthermore DNQX mediated LR elongation inhibition is reversed by L-Glu. This data further validate the conclusion that AtGLRs play a role in N sensing and LR elongation.

Plant hormones such as auxins and abscisic acid (ABA) are known to play a role in N induced LR growth and inhibition (Zhang et al. 1999. PNAS USA. 99:6529-34). Auxins induce primary and lateral root growth at a lower concentration. However at a higher concentration auxins are inhibitory on the growth of primary root. ABA inhibits the growth of PR and LR and nitrate at 50 mM concentration inhibits PR and LR by accumulating ABA (Signora et al. 2001. Plant J. 28:655).

To assess the role of auxins in the AtGLR response, the effect of DNQX on auxin levels were evaluated. Auxin responsive reporter plants carrying the expression system DR5::GUS were used in the histochemical assays. When incubated with 400 μM DNQX, DR5::GUS seedlings demonstrated inhibition of LR and PR elongation. Microscopic examination after GUS staining for 10 hrs revealed that DNQX treated plants had higher levels of auxins in PR and LR primordia compared to control plants (FIG. 9) suggesting that DNQX induced inhibition is mediated by hyperaccumulation of auxins. Similar results were reported in phosphate starvation studies (Nacry et al. 2005 Plant Physiol. 138:2061).

The ability of L-Glu to reverse the DNQX mediated inhibition demonstrates that N may be sensed as L-Glu or an endogenous ligand but not as nitrate. Many of the bioactive iGLR agonists were identified from plants such as kainite from seaweed *Digenea simplex*, quisqualic acid found in *Quisqualis indica* seeds, —N-methyl-amino-7 L-alanine (BMAA) produced in cycads and —N-oxalylamino-L-alanine (BOAA) from chickpeas (Adams and Swanson, 1996. Trends in Neurosci (Suppl.) 20).

Our findings show, when plants sense N starvation, as mimicked by DNQX treatment (FIG. 8 and FIG. 9) they exhibit inhibition of LR elongation. Since phosphate starvation and N starvation result in similar phenotype, including hyper accumulation of auxins, AtGLRs may also co-ordinate signaling processes involved in phosphate sensing.

Immunoblot analyses were used to validate the conclusion that AtGLRs mediate N sensing and antiAtGLR3.2 plants have increased N sensing. N induces the genes involved in its absorption and assimilation. One of the first steps in the assimilation of N is the incorporation of ammonium into amino acids by the GS/GOGAT pathway. In order to assess the improved assimilation of ammonium in antiAtGLR3.2 plants, we determined the accumulation of enzymes involved in N assimilation such as the levels of glutamine synthetase (GS), cytoplasmic aspartate amino transferase (AAT2) and ferredoxin dependent glutamine-2-oxoglutarate aminotransferase (Fd-GOGAT) using immunoblot analysis (FIG. 12). The antiAtGLR3.2 plants had increased levels of GS1, GS2, AAT2 and Fd-GOGAT when compared with WT. The antiAtGLR1.1 plants had reduced levels of GS, AAT2 and Fd. GOGAT (Kang and Turano. 2003. PNAS. 100: 6872). Thus antiAtGLR3.2 plants with their increased N sensing (FIG. 3) have induced levels of enzymes involved in N assimilation (FIG. 12), while antiAtGLR1.1 plants with the reduced levels of N sensing had the enzymes involved in N assimilation down regulated. Plants that over express GS, AS or GOGAT also demonstrated improvements in amino acids, protein content, plant growth and yield levels (U.S. Pat. No. 6,864,405).

In plants stomatal conductance effects the exchange of $CO_2$ and $O_2$, for respiration and photosynthesis, respectively as well as loss of water due to transpiration (Maser et al. 2003 The *Arabidopsis* book). Endogenous N levels are known to modify stomatal conductance (Ebdon et al. 1999. Crop Sci. 39:209). The antiAtGLR1.1 plants are known to have reduced levels of stomatal conductance (Kang et al. 2004 Pl. Cell Physiol. 45:1380-1389) because they utilize less water. Drought stress analyses of antiAtGLR3.2 plants demonstrated that they have increased stomatal conductance. Thus AtGLRs can also be used to modulate the stomatal conductance of plants based on the N status (FIG. 10).

Phenotypic analyses of antiAtGLR3.2 plants demonstrated that they have increased biomass production (FIG. 11, 13). In the field increased levels of N application improve plant biomass and yield levels. Similarly increased levels of major N assimilation enzymes such as GS-GOGAT enzymes were shown to improve plant biomass production and yield (U.S. Pat. No. 6,864,405). By improving the N sensing, AtGLRs constitute an important component that regulate diverse processes such as N absorption, assimilation, plant growth and yield. Regulation of these receptors offers potential to improve nutritional value, biomass, and yield in crop plants. By regulating these receptors improvements in the N use efficiency and hence improvements in the efficiency of crop production can be achieved.

It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

We claim:

1. A method for developing a plant comprising (i) selecting a progenitor plant for which improved biomass production is desired, and (ii) introducing into the plant a nucleic acid molecule that encodes an RNA antisense sufficient to reduce levels of AtGLR3.2 and increase biomass of said plant relative to said progenitor plant.

2. The method of claim 1, comprising introducing into the plant an expression cassette, the expression cassette comprising a promoter operably linked to the nucleic acid molecule that encodes the RNA antisense.

3. The method of claim 2, wherein the promoter is tissue-specific.

4. The method of claim 2, wherein the promoter is inducible.

5. The method of claim 1, wherein the plant exhibits increased levels of GS, AAT, and Fd-GOGAT compared to a progenitor plant that does not contain the RNA antisense.

6. The method of claim 1, wherein the plant exhibits one or more traits selected from: i) faster rate of growth, ii) greater fresh or dry weight at maturation, iii) greater fruit or seed yield, iv) greater free amino acid content in the whole plant, v) greater free amino acid content in the fruit or seed, vi) greater protein content in seed or fruit, vii) greater protein content in a vegetative tissue, or viii) greater amount of one or more of oils, polymers, or enzymes, than a progenitor plant which does not contain the nucleic acid molecule that encodes the RNA antisense.

7. The method of claim 1, wherein the plant has increased stomatal conductance and increased transpirational loss compared to a progenitor plant that does not contain the nucleic acid molecule that encodes the RNA antisense.

8. A method for developing a plant comprising introducing into a plant a nucleic acid molecule that encodes an RNA antisense with at least 92% sequence identity to the RNA antisense to SEQ ID NO: 2, whereby AtGLR3.2 is down regulated.

9. The method of claim 8, comprising introducing into the plant an expression cassette, the expression cassette comprising a promoter operably linked to the nucleic acid molecule that encodes the RNA antisense with at least 92% sequence identity to the RNA antisense to SEQ ID NO: 2.

10. The method of claim 1, further comprising the step of selecting for a plant that exhibits increased levels of primary root and lateral root growth compared to a progenitor plant that does not contain the nucleic acid molecule that encodes the RNA antisense.

11. The method of claim 1, further comprising the step of selecting for a plant that exhibits increased levels of GS, AAT, or Fd-GOGAT compared to a progenitor plant that does not contain the nucleic acid molecule that encodes the RNA antisense.

12. The method of claim 1, further comprising the step of selecting for a plant that exhibits at least one of the following characteristics when compared to a progenitor plant that does not contain the nucleic acid molecule that encodes the RNA antisense:
- faster rate of growth;
- greater fresh or dry weight at maturation;
- greater fruit or seed yield;
- greater free amino acid content in the whole plant;
- greater free amino acid content in the fruit or seed;
- greater protein content in seed or fruit; and
- greater protein content in a vegetative tissue.

13. The method of claim 2, wherein the plant exhibits one or more traits selected from: i) faster rate of growth, ii) greater fresh or dry weight at maturation, iii) greater fruit or seed yield, iv) greater free amino acid content in the whole plant, v) greater free amino acid content in the fruit or seed, vi) greater protein content in seed or fruit, vii) greater protein content in a vegetative tissue, or viii) greater amount of one or more of oils, polymers, or enzymes, than a progenitor plant which does not contain the nucleic acid molecule that encodes the RNA antisense.

* * * * *

SEQUENCE LISTING

<160> NUMBER OF SEQ ID NOS: 4

<210> SEQ ID NO 1
<211> LENGTH: 2641
<212> TYPE: DNA
<213> ORGANISM: Arabidopsis thaliana

<400> SEQUENCE: 1

```
aagcgaacgt tacagagcta taaagaaat tatatggaga ttctgttttc tatttccatt      60
cttgctcttc tcttttccgg agtagtagct gctccaagcg acgatgatgt tttcgaagag     120
gttagggttg gattggtggt tgacttgagt tctattcaag gcaagattct ggaaacttct     180
tttaacttag cgctttcaga tttctatggc atcaacaatg gataccgaac cagagtctct     240
gttttggtca gagactccca aggagacccg atcattgctc ttgccgccgc tactgatctt     300
ctcaaaaatg caaaagcgga agccattgtt ggtgcacaat cattacaaga ggcaaagctt     360
ttggcgacga ttagcgaaaa agctaaagtt ccggtcatat ctactttctt gccaaacacg     420
ttatctttga agaaatacga taactttatt caatggacgc atgatactac atcagaggct     480
aagggaatta caagtctcat acaagatttc agttgtaaat cggttgtggt tatatacgag     540
gatgctgatg attggagtga gagtttgcaa atattggttg agaattttca agataaagga     600
atctatatcg ctcgttctgc ttcttttgca gtctcatcat caggagaaaa tcatatgatg     660
aatcagctaa ggaagcttaa ggtctcaaga gcatcggttt ttgtggtgca tatgtccgag     720
attcttgttt ctcgtctctt ccaatgtgta gagaagttag gtttgatgga agaagcgttc     780
gcttggatcc tcactgcaag aaccatgaac tacttggaac attttgcaat aactaggtcg     840
atgcaagggg tcattggttt caaatcttac atccctgtat ctgaagaagt taagaatttt     900
acttcaagat tgaggaaacg tatgggagat gatacagaaa cagagcattc tagtgtaatc     960
atcggtttac gcgcacacga tatcgcttgt attctagcaa atgcagtaga gaagttcagt    1020
gtaagtggta aagttgaagc atcttcgaat gtatcagctg atcttctgga tacaattaga    1080
catagtagat tcaagggttt gagtggtgac atccaaatct ctgacaacaa atttatctca    1140
gagacatttg aaatcgtgaa tattggaaga gaaaaacaga gaaggatagg attatggagt    1200
ggtggtagtt ttagccaaag aagacagatt gtttggcctg gcaggtctcg taagatccca    1260
```

| | | | | |
|---|---|---|---|---|
| agacaccgtg | ttttggcaga | gaaaggtgaa | aagaaggtgc | ttagggtctt | agttaccgca | 1320 |
| ggaaacaagg | tcccgcatct | agtgtcggtg | cgtcctgatc | ctgaaacagg | tgttaatact | 1380 |
| gtctctggat | tctgcgtaga | ggttttcaag | acttgcattg | ctccttttaa | ctacgagctt | 1440 |
| gaattcatac | cttaccgtgg | aaacaatgac | aatcttgctt | atctactttc | tactcagaga | 1500 |
| gacaagtatg | atgcagcagt | tggtgatatc | accatcactt | ccaacagatc | tttgtatgtt | 1560 |
| gattttactt | tgccgtacac | tgacattggt | attggaatcc | tgacagtaaa | aagaaaagc | 1620 |
| caagggatgt | ggactttctt | tgatcctttt | gaaaaatcct | tgtggctagc | gagtggagct | 1680 |
| ttcttcgtct | tgaccgggat | tgttgttggt | tggttgaac | ggcccgttaa | tccggagttt | 1740 |
| caaggctctt | ggggacaaca | acttagtatg | atgctctggt | ttggattctc | taccattgtg | 1800 |
| tttgctcaca | gggagaagct | acagaaaatg | tcatcaagat | tcttagtcat | agtttgggtt | 1860 |
| tttgtggtgt | taatattgac | ttcaagttac | agcgcaaact | tgacatcaac | caagaccatt | 1920 |
| tctcgcatgc | aattaaatca | tcagatggtt | ttcggggat | ctacgacgtc | aatgactgcg | 1980 |
| aagctcggat | ccattaatgc | agttgaggcc | tatgcacaac | ttttgcgaga | tggaactctt | 2040 |
| aatcatgtca | tcaatgaaat | accttatctc | agtatcctta | tcggaaatta | tccgaatgat | 2100 |
| ttcgtaatga | cagatagagt | gactaatacc | aatggctttg | gctttatgtt | ccagaaaggt | 2160 |
| tcggatttgg | ttcctaaagt | atcgcgagaa | atcgcgaagc | taagatcatt | gggaatgttg | 2220 |
| aaagacatgg | agaaaaaatg | gtttcaaaag | ctggattcac | taaatgtaca | ttccaacact | 2280 |
| gaggaagttg | cctctaccaa | cgacgatgat | gaggcatcta | agcgattcac | cttccgtgag | 2340 |
| ttgcgcggtt | tgttcatcat | tgcgggagct | gctcatgttc | tcgtactagc | cctacatctc | 2400 |
| tttcatacgc | gtcaagaggt | atcacgacta | tgcaccaaac | ttcaaagctt | ctataagtaa | 2460 |
| aaagtgatcc | atcattcata | agctctacta | tagcaattga | tggaggactc | ataagtaaca | 2520 |
| acaaagtaca | cttcgaaaca | aatgtcacat | gtaatacttg | gtttttttc | ccgtttaaat | 2580 |
| tcacatgtaa | taatttaact | cacgtaaata | ctaaagtgat | tcacccaaaa | aaaaaaaaa | 2640 |
| a | | | | | 2641 |

<210> SEQ ID NO 2
<211> LENGTH: 3005
<212> TYPE: DNA
<213> ORGANISM: Arabidopsis thaliana

<400> SEQUENCE: 2

| | | | | | |
|---|---|---|---|---|---|
| ggtgtttcag | gaactgatta | agccaaagct | atgttttggg | ttttggttct | gttgagcttc | 60 |
| attgttctta | ttggtgatgg | gatgatttca | gagggagctg | gtttaaggcc | tcgttatgtt | 120 |
| gatgttggag | caatattcag | tttagggact | ttacagggtg | aagttacaaa | tattgctatg | 180 |
| aaagctgcag | aggaagatgt | aaattctgat | cctagcttcc | ttggtggatc | aaaattgcgt | 240 |
| ataacgacgt | atgatgcaaa | gcgtaatgga | ttcctcacca | tcatgggagc | tttgcaattc | 300 |
| atggagactg | atgctgtggc | tatcattggt | cctcagacat | caataatggc | tcatgtactg | 360 |
| tctcatcttg | caaatgagct | tagtgtgcct | atgttgtcat | tcacagcttt | agaccctagt | 420 |
| ctctcggcgc | ttcagttccc | gttctttgtc | cagacagcac | ctagtgatct | ctttctgatg | 480 |
| cgtgccattg | cggaaatgat | aagttactac | ggttggtcag | aggtgattgc | attgtataat | 540 |
| gatgatgaca | acagtagaaa | cggtataaca | gctttaggcg | atgagctcga | aggaaggcgc | 600 |
| tgcaagattt | catacaaggc | tgtgcttcct | ttggatgtgg | tgattacgag | tcctcgtgag | 660 |
| attataaatg | agttggttaa | gattcaaggg | atggaatctc | gggtaatcat | tgtgaacact | 720 |

```
ttccctaaaa caggtaagaa aatctttgag gaagcccaga agcttggcat gatggagaaa    780
ggctatgttt ggatagctac aacttggttg acttctctgt tagattctgt taacccgtta    840
cctgccaaga ctgctgaatc tcttagaggc gtgcttactc ttcgtattca cacgccaaat    900
tcaaaaaaga aaaagatttc cgtggcacgg tggaacaagt tgagtaacgg gactgtcggt    960
ttaaacgttt atggtctcta tgcttatgat actgtctgga tcattgctcg agctgttaag   1020
agacttctag atagcagagc taacatttcc ttctctagtg acccaaagtt aaccagcatg   1080
aagggaggag ggtcactgaa tctaggtgca ttgagcatat ttgaccaagg atcacaattt   1140
cttgattata ttgtgaatac aaatatgact ggtgttacag gtcaaataca gtttcttcct   1200
gacagatcaa tgatacagcc ctcatatgac atcataaacg tggttgatga cgggtttagg   1260
cagatagggt attggtctaa ccattccggg ctctctatta tacctccaga gtcactatac   1320
aaaaagcttt caaatcgttc gagctcaaac caacatctga acaatgtgac ttggcctggt   1380
gggacttctg agacaccacg tggttgggtt tttcctaaca cgggagacg attgagaatc    1440 ggtgtacccg atagagcaag ttttaaggag tttgtgtcaa ggttggatgg aagcaacaaa   1500
gtgcaagggt atgccattga tgtctttgaa gctgcggtaa aactgatttc ttatccggtt   1560
cctcatgagt tcgtcctatt tggagacggt ctcaagaacc caaacttcaa tgaatttgtc   1620
aacaatgtca ctattggggt atttgatgct gttgtaggag acatagctat tgttacgaaa   1680
cgaacaagga ttgtggattt cactcagcct tacatagaat cagggcttgt cgtggttgct   1740
cctgtcacaa agctaaatga tactccgtgg gcgttttac gcccttttac acctccaatg    1800
tgggctgtta cagcagcttt tttcctcatc gttggatcag taatatggat tcttgaacat   1860
agaatcaacg atgagttccg cggacctcca aggaaacaaa ttgttactat tctctggttc   1920
agcttctcca cgatgttttt ctcccacaga gagaacacag tgagtacact cggtcgtgct   1980
gttctgctca tctggctatt tgtggtacta atcataacat caagctacac agcgagtctt   2040
acatcgattc ttacagtgca acagctaaac tcaccaatca gaggagtaga cacactcatc   2100
agcagcagtg gacgagttgg gtttcaggta ggttcttatg cagaaaacta catgattgat   2160
gagcttaaca ttgccagatc cagacttgta ccactcggct ctcctaaaga atacgctgca   2220
gctcttcaaa acggaactgt tgctgcaatt gttgatgagc gtccttacgt tgatctcttc   2280
ctctcagaat tctgcggatt tgccattaga ggccaagaat tcaccagaag tggctgggga   2340
tttgcatttc caagagactc tccattagca atcgacatgt caaccgcgat cttaggtcta   2400
tcagaaaccg gacagcttca aaagatccat gacaagtggc tttcaagatc taactgcagt   2460
aacctcaacg gttcagtgtc agatgaagat tcagaacagc ttaaactccg aagcttctgg   2520
ggattattcc ttgtgtgtgg gatctcttgt tttatcgctc tcttcatcta cttcttcaag   2580
atagtccgcg acttcttccg ccacggcaaa tatgatgaag aagccacagt atcttcacca   2640
gaaagttcac gttctaaatc attgcagaca tttctagctt atttttgatga aaagaagac    2700 gaatccaaga gaaggatgaa gcgtaaacga aacgatgatc tttctttaaa gccttctaga   2760
ccaatatgac agatccatca agactcaagc atgaaagatg aagaaatgca gacacacatc   2820
ctcatactta tatagtagaa tgcagatttt gattttaact gtacttcaag aataataagc   2880
cttgaagaat acggaacatt ttttaaccaa agaaagtgaa gcataaactt gtaagacaaa   2940
gctatatcat acatagttct taaaaaaaac aattacttgg tatccttttt ttttttttt    3000 ttttt                                                              3005
```

<210> SEQ ID NO 3
<211> LENGTH: 808
<212> TYPE: PRT
<213> ORGANISM: Arabidopsis thaliana

<400> SEQUENCE: 3

```
Met Glu Ile Leu Phe Ser Ile Ser Ile Leu Ala Leu Leu Phe Ser Gly
1               5                   10                  15

Val Val Ala Ala Pro Ser Asp Asp Val Phe Glu Glu Val Arg Val
            20                  25                  30

Gly Leu Val Val Asp Leu Ser Ser Ile Gln Gly Lys Ile Leu Glu Thr
        35                  40                  45

Ser Phe Asn Leu Ala Leu Ser Asp Phe Tyr Gly Ile Asn Asn Gly Tyr
    50                  55                  60

Arg Thr Arg Val Ser Val Leu Val Arg Asp Ser Gln Gly Asp Pro Ile
65                  70                  75                  80

Ile Ala Leu Ala Ala Ala Thr Asp Leu Leu Lys Asn Ala Lys Ala Glu
                85                  90                  95

Ala Ile Val Gly Ala Gln Ser Leu Gln Glu Ala Lys Leu Leu Ala Thr
            100                 105                 110

Ile Ser Glu Lys Ala Lys Val Pro Val Ile Ser Thr Phe Leu Pro Asn
        115                 120                 125

Thr Leu Ser Leu Lys Lys Tyr Asp Asn Phe Ile Gln Trp Thr His Asp
    130                 135                 140

Thr Thr Ser Glu Ala Lys Gly Ile Thr Ser Leu Ile Gln Asp Phe Ser
145                 150                 155                 160

Cys Lys Ser Val Val Ile Tyr Glu Asp Ala Asp Trp Ser Glu
                165                 170                 175

Ser Leu Gln Ile Leu Val Glu Asn Phe Gln Asp Lys Gly Ile Tyr Ile
            180                 185                 190

Ala Arg Ser Ala Ser Phe Ala Val Ser Ser Ser Gly Glu Asn His Met
        195                 200                 205

Met Asn Gln Leu Arg Lys Leu Lys Val Ser Arg Ala Ser Val Phe Val
    210                 215                 220

Val His Met Ser Glu Ile Leu Val Ser Arg Leu Phe Gln Cys Val Glu
225                 230                 235                 240

Lys Leu Gly Leu Met Glu Glu Ala Phe Ala Trp Ile Leu Thr Ala Arg
                245                 250                 255

Thr Met Asn Tyr Leu Glu His Phe Ala Ile Thr Arg Ser Met Gln Gly
            260                 265                 270

Val Ile Gly Phe Lys Ser Tyr Ile Pro Val Ser Glu Val Lys Asn
        275                 280                 285

Phe Thr Ser Arg Leu Arg Lys Arg Met Gly Asp Thr Glu Thr Glu
    290                 295                 300

His Ser Ser Val Ile Ile Gly Leu Arg Ala His Asp Ile Ala Cys Ile
305                 310                 315                 320

Leu Ala Asn Ala Val Glu Lys Phe Ser Val Ser Gly Lys Val Glu Ala
                325                 330                 335

Ser Ser Asn Val Ser Ala Asp Leu Leu Asp Thr Ile Arg His Ser Arg
            340                 345                 350

Phe Lys Gly Leu Ser Gly Asp Ile Gln Ile Ser Asp Asn Lys Phe Ile
        355                 360                 365

Ser Glu Thr Phe Glu Ile Val Asn Ile Gly Arg Glu Lys Gln Arg Arg
    370                 375                 380
```

```
Ile Gly Leu Trp Ser Gly Gly Ser Phe Ser Gln Arg Gln Ile Val
385                 390                 395                 400

Trp Pro Gly Arg Ser Arg Lys Ile Pro Arg His Arg Val Leu Ala Glu
            405                 410                 415

Lys Gly Glu Lys Lys Val Leu Arg Val Leu Val Thr Ala Gly Asn Lys
        420                 425                 430

Val Pro His Leu Val Ser Val Arg Pro Asp Pro Glu Thr Gly Val Asn
    435                 440                 445

Thr Val Ser Gly Phe Cys Val Glu Val Phe Lys Thr Cys Ile Ala Pro
450                 455                 460

Phe Asn Tyr Glu Leu Glu Phe Ile Pro Tyr Arg Gly Asn Asn Asp Asn
465                 470                 475                 480

Leu Ala Tyr Leu Leu Ser Thr Gln Arg Asp Lys Tyr Asp Ala Ala Val
            485                 490                 495

Gly Asp Ile Thr Ile Thr Ser Asn Arg Ser Leu Tyr Val Asp Phe Thr
        500                 505                 510

Leu Pro Tyr Thr Asp Ile Gly Ile Gly Ile Leu Thr Val Lys Lys Lys
            515                 520                 525

Ser Gln Gly Met Trp Thr Phe Phe Asp Pro Glu Lys Ser Leu Trp
530                 535                 540

Leu Ala Ser Gly Ala Phe Phe Val Leu Thr Gly Ile Val Val Trp Leu
545                 550                 555                 560

Val Glu Arg Pro Val Asn Pro Glu Phe Gln Gly Ser Trp Gly Gln Gln
            565                 570                 575

Leu Ser Met Met Leu Trp Phe Gly Phe Ser Thr Ile Val Phe Ala His
            580                 585                 590

Arg Glu Lys Leu Gln Lys Met Ser Ser Arg Phe Leu Val Ile Val Trp
        595                 600                 605

Val Phe Val Val Leu Ile Leu Thr Ser Ser Tyr Ser Ala Asn Leu Thr
            610                 615                 620

Ser Thr Lys Thr Ile Ser Arg Met Gln Leu Asn His Gln Met Val Phe
625                 630                 635                 640

Gly Gly Ser Thr Thr Ser Met Thr Ala Lys Leu Gly Ser Ile Asn Ala
                645                 650                 655

Val Glu Ala Tyr Ala Gln Leu Leu Arg Asp Gly Thr Leu Asn His Val
            660                 665                 670

Ile Asn Glu Ile Pro Tyr Leu Ser Ile Leu Gly Asn Tyr Pro Asn
        675                 680                 685

Asp Phe Val Met Thr Asp Arg Val Thr Asn Thr Asn Gly Phe Gly Phe
        690                 695                 700

Met Phe Gln Lys Gly Ser Asp Leu Val Pro Lys Val Ser Arg Glu Ile
705                 710                 715                 720

Ala Lys Leu Arg Ser Leu Gly Met Leu Lys Asp Met Glu Lys Lys Trp
            725                 730                 735

Phe Gln Lys Leu Asp Ser Leu Asn Val His Ser Asn Thr Glu Val
            740                 745                 750

Ala Ser Thr Asn Asp Asp Glu Ala Ser Lys Arg Phe Thr Phe Arg
            755                 760                 765

Glu Leu Arg Gly Leu Phe Ile Ile Ala Gly Ala Ala His Val Leu Val
            770                 775                 780

Leu Ala Leu His Leu Phe His Thr Arg Gln Glu Val Ser Arg Leu Cys
785                 790                 795                 800
```

-continued

Thr Lys Leu Gln Ser Phe Tyr Lys
            805

<210> SEQ ID NO 4
<211> LENGTH: 912
<212> TYPE: PRT
<213> ORGANISM: Arabidopsis thaliana

<400> SEQUENCE: 4

Met Phe Trp Val Leu Val Leu Leu Ser Phe Ile Val Leu Ile Gly Asp
1               5                   10                  15

Gly Met Ile Ser Glu Gly Ala Gly Leu Arg Pro Arg Tyr Val Asp Val
            20                  25                  30

Gly Ala Ile Phe Ser Leu Gly Thr Leu Gln Gly Glu Val Thr Asn Ile
        35                  40                  45

Ala Met Lys Ala Ala Glu Glu Asp Val Asn Ser Asp Pro Ser Phe Leu
    50                  55                  60

Gly Gly Ser Lys Leu Arg Ile Thr Thr Tyr Asp Ala Lys Arg Asn Gly
65                  70                  75                  80

Phe Leu Thr Ile Met Gly Ala Leu Gln Phe Met Glu Thr Asp Ala Val
                85                  90                  95

Ala Ile Ile Gly Pro Gln Thr Ser Ile Met Ala His Val Leu Ser His
            100                 105                 110

Leu Ala Asn Glu Leu Ser Val Pro Met Leu Ser Phe Thr Ala Leu Asp
        115                 120                 125

Pro Ser Leu Ser Ala Leu Gln Phe Pro Phe Phe Val Gln Thr Ala Pro
    130                 135                 140

Ser Asp Leu Phe Leu Met Arg Ala Ile Ala Glu Met Ile Ser Tyr Tyr
145                 150                 155                 160

Gly Trp Ser Glu Val Ile Ala Leu Tyr Asn Asp Asp Asn Ser Arg
                165                 170                 175

Asn Gly Ile Thr Ala Leu Gly Asp Glu Leu Glu Gly Arg Arg Cys Lys
            180                 185                 190

Ile Ser Tyr Lys Ala Val Leu Pro Leu Asp Val Val Ile Thr Ser Pro
        195                 200                 205

Arg Glu Ile Ile Asn Glu Leu Val Lys Ile Gln Gly Met Glu Ser Arg
    210                 215                 220

Val Ile Ile Val Asn Thr Phe Pro Lys Thr Gly Lys Lys Ile Phe Glu
225                 230                 235                 240

Glu Ala Gln Lys Leu Gly Met Met Glu Lys Gly Tyr Val Trp Ile Ala
                245                 250                 255

Thr Thr Trp Leu Thr Ser Leu Leu Asp Ser Val Asn Pro Leu Pro Ala
            260                 265                 270

Lys Thr Ala Glu Ser Leu Arg Gly Val Leu Thr Leu Arg Ile His Thr
        275                 280                 285

Pro Asn Ser Lys Lys Lys Asp Phe Val Ala Arg Trp Asn Lys Leu
    290                 295                 300

Ser Asn Gly Thr Val Gly Leu Asn Val Tyr Gly Leu Tyr Ala Tyr Asp
305                 310                 315                 320

Thr Val Trp Ile Ile Ala Arg Ala Val Lys Arg Leu Leu Asp Ser Arg
                325                 330                 335

Ala Asn Ile Ser Phe Ser Ser Asp Pro Lys Leu Thr Ser Met Lys Gly
            340                 345                 350

Gly Gly Ser Leu Asn Leu Gly Ala Leu Ser Ile Phe Asp Gln Gly Ser
        355                 360                 365

```
Gln Phe Leu Asp Tyr Ile Val Asn Thr Asn Met Thr Gly Val Thr Gly
    370                 375                 380

Gln Ile Gln Phe Leu Pro Asp Arg Ser Met Ile Gln Pro Ser Tyr Asp
385                 390                 395                 400

Ile Ile Asn Val Val Asp Asp Gly Phe Arg Gln Ile Gly Tyr Trp Ser
            405                 410                 415

Asn His Ser Gly Leu Ser Ile Ile Pro Pro Glu Ser Leu Tyr Lys Lys
            420                 425                 430

Leu Ser Asn Arg Ser Ser Ser Asn Gln His Leu Asn Asn Val Thr Trp
        435                 440                 445

Pro Gly Gly Thr Ser Glu Thr Pro Arg Gly Trp Val Phe Pro Asn Asn
    450                 455                 460

Gly Arg Arg Leu Arg Ile Gly Val Pro Asp Arg Ala Ser Phe Lys Glu
465                 470                 475                 480

Phe Val Ser Arg Leu Asp Gly Ser Asn Lys Val Gln Gly Tyr Ala Ile
            485                 490                 495

Asp Val Phe Glu Ala Ala Val Lys Leu Ile Ser Tyr Pro Val Pro His
            500                 505                 510

Glu Phe Val Leu Phe Gly Asp Gly Leu Lys Asn Pro Asn Phe Asn Glu
    515                 520                 525

Phe Val Asn Asn Val Thr Ile Gly Val Phe Asp Ala Val Val Gly Asp
    530                 535                 540

Ile Ala Ile Val Thr Lys Arg Thr Arg Ile Val Asp Phe Thr Gln Pro
545                 550                 555                 560

Tyr Ile Glu Ser Gly Leu Val Val Ala Pro Val Thr Lys Leu Asn
            565                 570                 575

Asp Thr Pro Trp Ala Phe Leu Arg Pro Phe Thr Pro Met Trp Ala
        580                 585                 590

Val Thr Ala Ala Phe Phe Leu Ile Val Gly Ser Val Ile Trp Ile Leu
        595                 600                 605

Glu His Arg Ile Asn Asp Glu Phe Arg Gly Pro Pro Arg Lys Gln Ile
    610                 615                 620

Val Thr Ile Leu Trp Phe Ser Phe Ser Thr Met Phe Phe Ser His Arg
625                 630                 635                 640

Glu Asn Thr Val Ser Thr Leu Gly Arg Ala Val Leu Leu Ile Trp Leu
            645                 650                 655

Phe Val Val Leu Ile Ile Thr Ser Ser Tyr Thr Ala Ser Leu Thr Ser
            660                 665                 670

Ile Leu Thr Val Gln Gln Leu Asn Ser Pro Ile Arg Gly Val Asp Thr
        675                 680                 685

Leu Ile Ser Ser Ser Gly Arg Val Gly Phe Gln Val Gly Ser Tyr Ala
    690                 695                 700

Glu Asn Tyr Met Ile Asp Glu Leu Asn Ile Ala Arg Ser Arg Leu Val
705                 710                 715                 720

Pro Leu Gly Ser Pro Lys Glu Tyr Ala Ala Ala Leu Gln Asn Gly Thr
            725                 730                 735

Val Ala Ala Ile Val Asp Glu Arg Pro Tyr Val Asp Leu Phe Leu Ser
            740                 745                 750

Glu Phe Cys Gly Phe Ala Ile Arg Gly Gln Glu Phe Thr Arg Ser Gly
        755                 760                 765

Trp Gly Phe Ala Phe Pro Arg Asp Ser Pro Leu Ala Ile Asp Met Ser
    770                 775                 780
```

-continued

```
Thr Ala Ile Leu Gly Leu Ser Glu Thr Gly Gln Leu Gln Lys Ile His
785             790             795             800

Asp Lys Trp Leu Ser Arg Ser Asn Cys Ser Asn Leu Asn Gly Ser Val
            805             810             815

Ser Asp Glu Asp Ser Glu Gln Leu Lys Leu Arg Ser Phe Trp Gly Leu
            820             825             830

Phe Leu Val Cys Gly Ile Ser Cys Phe Ile Ala Leu Phe Ile Tyr Phe
        835             840             845

Phe Lys Ile Val Arg Asp Phe Phe Arg His Gly Lys Tyr Asp Glu Glu
    850             855             860

Ala Thr Val Ser Ser Pro Glu Ser Ser Arg Ser Lys Ser Leu Gln Thr
865             870             875             880

Phe Leu Ala Tyr Phe Asp Glu Lys Glu Asp Glu Ser Lys Arg Arg Met
            885             890             895

Lys Arg Lys Arg Asn Asp Asp Leu Ser Leu Lys Pro Ser Arg Pro Ile
            900             905             910
```